United States Patent
Kusuhara et al.

(10) Patent No.: US 10,890,593 B2
(45) Date of Patent: Jan. 12, 2021

(54) TEST PIECE MOUNTING BODY, TRANSPORT UNIT, AND TEST PIECE ANALYZER

(71) Applicant: Sysmex Corporation, Kobe (JP)

(72) Inventors: Takashi Kusuhara, Tokyo (JP); Satoshi Hayashi, Ishikawa (JP)

(73) Assignee: SYSMEX CORPORATION, Hyogo (JP)

( * ) Notice: Subject to any disclaimer, the term of this patent is extended or adjusted under 35 U.S.C. 154(b) by 125 days.

(21) Appl. No.: 15/287,133

(22) Filed: Oct. 6, 2016

(65) Prior Publication Data

US 2017/0102402 A1    Apr. 13, 2017

(30) Foreign Application Priority Data

Oct. 9, 2015 (JP) .................... 2015-201503
Oct. 9, 2015 (JP) .................... 2015-201504

(51) Int. Cl.

| | |
|---|---|
| *G01N 35/10* | (2006.01) |
| *G01N 35/00* | (2006.01) |
| *G01N 35/04* | (2006.01) |
| *B01L 9/00* | (2006.01) |
| *G01N 33/493* | (2006.01) |

(Continued)

(52) U.S. Cl.
CPC ............ *G01N 35/10* (2013.01); *B01L 9/52* (2013.01); *G01N 33/493* (2013.01); *G01N 33/84* (2013.01); *G01N 35/00029* (2013.01); *G01N 35/04* (2013.01); *B01L 2300/0825* (2013.01); *G01N 33/4875* (2013.01); *G01N 35/021* (2013.01);

(Continued)

(58) Field of Classification Search
CPC .......................................................... B01L 9/52
See application file for complete search history.

(56) References Cited

U.S. PATENT DOCUMENTS 3,856,051 A * 12/1974 Bain ................... A61M 16/009
138/114
3,859,051 A * 1/1975 Natelson ............ G01N 35/1097
422/64

(Continued)

FOREIGN PATENT DOCUMENTS

| CN | 201408197 Y | 2/2010 |
|---|---|---|
| CN | 101960311 A | 1/2011 |

(Continued)

OTHER PUBLICATIONS

Pamphlet of Automated Urine Analyzer US-2200, Eiken Chemical Co., Ltd., Teramecs Co., Ltd., Jul. 2013, p.1 to p. 2, http://www.eiken.co.jp/products_technique/medical_device/pdf/M-8J00.pdf; Cited in the Japanese Office Action dated Apr. 16, 2019 in a counterpart Japanese patent application.

(Continued)

*Primary Examiner* — Matthew D Krcha
(74) *Attorney, Agent, or Firm* — Brinks Gilson & Lione

(57) ABSTRACT

A test piece analyzer capable of easily washing a transport device to which the sample (urine sample) has adhered is provided. A test piece analyzer is provided with a transport unit having a transport device to transport a test piece, a drive part to drive the transport device, an imaging unit to image the test piece, and a casing to house the transport unit, imaging unit, and drive part. The transport unit is removable relative to the casing.

16 Claims, 18 Drawing Sheets

(51) Int. Cl.
  *G01N 33/84*  (2006.01)
  *G01N 33/487* (2006.01)
  *G01N 35/02*  (2006.01)

(52) U.S. Cl.
  CPC .............. *G01N 2035/00039* (2013.01); *G01N 2035/00326* (2013.01); *G01N 2035/1062* (2013.01)

(56) References Cited

U.S. PATENT DOCUMENTS

| | | | | |
|---|---|---|---|---|
| 4,750,035 | A | * | 6/1988 | Chang .................... G01N 21/90 250/223 B |
| 4,960,566 | A | * | 10/1990 | Mochida ................. B01L 9/065 422/503 |
| 5,090,568 | A | * | 2/1992 | Tse ...................... A61B 10/0096 206/456 |
| 5,672,512 | A | * | 9/1997 | Shaw ............... G01N 35/00029 198/801 |
| 6,129,428 | A | * | 10/2000 | Helwig ..................... B01L 1/00 312/114 |
| 2005/0186114 | A1 | | 8/2005 | Reinhardt et al. |
| 2011/0000763 | A1 | * | 1/2011 | Kimura .................. G01N 35/04 198/340 |
| 2012/0075695 | A1 | | 3/2012 | DeBlasis et al. |
| 2012/0163680 | A1 | * | 6/2012 | Lefebvre ................ G01N 1/312 382/128 |
| 2014/0051156 | A1 | * | 2/2014 | Miyake .................. G01N 21/01 435/288.7 |
| 2014/0086808 | A1 | | 3/2014 | Itoh |
| 2015/0031135 | A1 | | 1/2015 | Zimmerle et al. |

FOREIGN PATENT DOCUMENTS

| | | | |
|---|---|---|---|
| CN | 102565428 | A | 7/2012 |
| CN | 104108562 | A | 10/2014 |
| CN | 104160251 | A | 11/2014 |
| EP | 2 472 265 | A2 | 7/2012 |
| JP | S58-21567 | A | 2/1983 |
| JP | 07005110 | A * | 1/1995 |
| JP | H7-5110 | A | 1/1995 |
| JP | 2005-090969 | A | 4/2005 |
| JP | 2005-098937 | A | 4/2005 |
| JP | 2005-127803 | A | 5/2005 |
| JP | 2009-229233 | A | 10/2009 |
| JP | 2012-141287 | A | 7/2012 |
| JP | 2014-77772 | A | 5/2014 |
| JP | 2015-510131 | A | 4/2015 |
| WO | WO 2011/122562 | A1 | 10/2011 |

OTHER PUBLICATIONS

Japanese Office Action dated Apr. 16, 2019 in a counterpart Japanese patent application No. 2015-201503.
Chinese Office Action dated Sep. 30, 2019 in a counterpart Chinese patent application No. 201610880274.3.
Chinese Office Action dated Feb. 11, 2019 in a counterpart Chinese patent application No. 201610880274.3.
Chinese Office Action dated Mar. 11, 2020 in a counterpart Chinese patent application No. 201610880274.3.
Chinese Office Action dated Oct. 16, 2020 in a counterpart Chinese patent application No. 201610880274.3.

* cited by examiner

FIG. 6
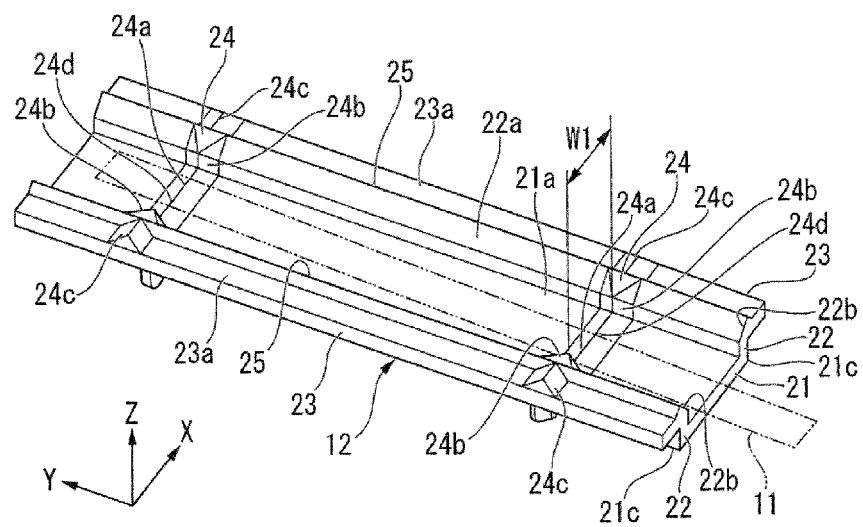
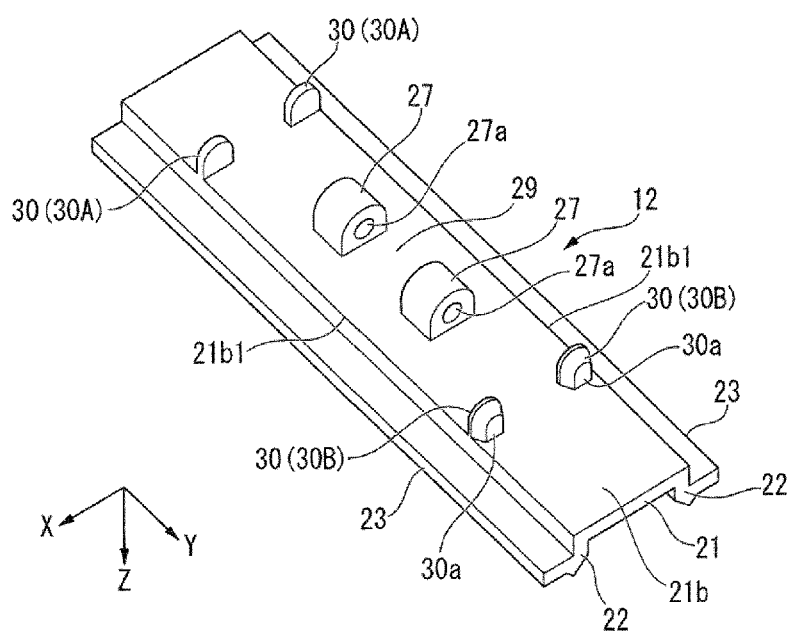
FIG. 7

FIG. 8
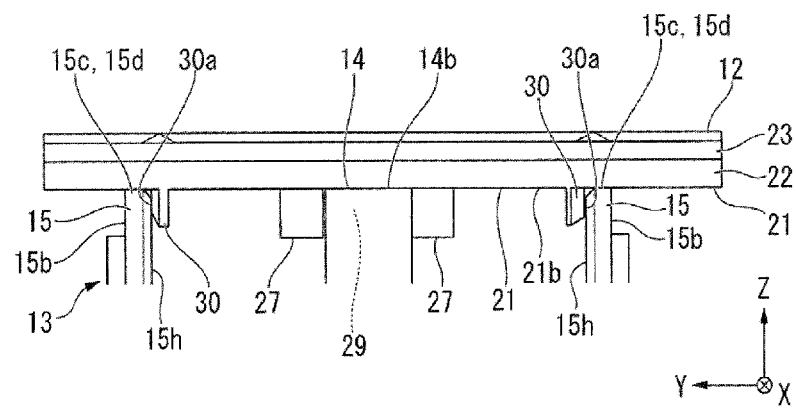
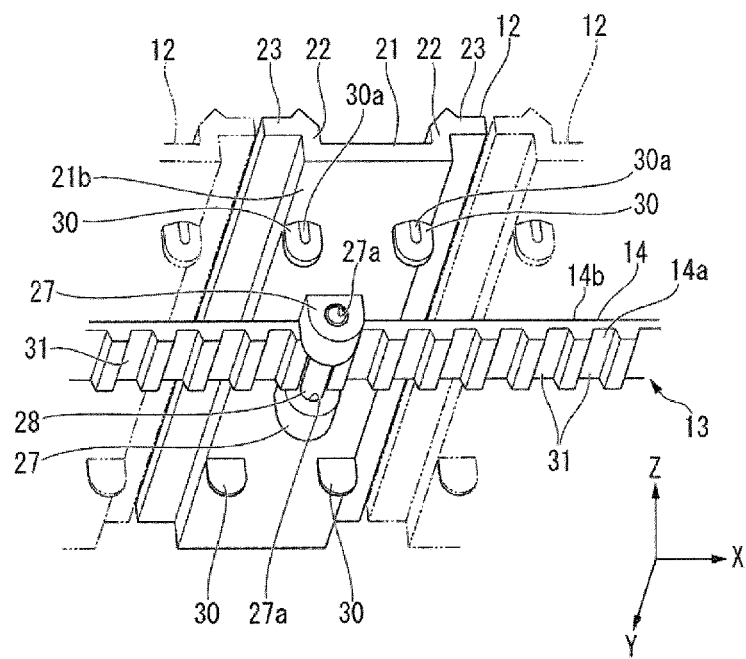
FIG. 9

TEST PIECE MOUNTING BODY, TRANSPORT UNIT, AND TEST PIECE ANALYZER

RELATED APPLICATIONS

This application claims priority from prior Japanese Patent Applications No. 2015-201503, filed on Oct. 9, 2015, entitled "Transport Unit And Test Piece Analysis Device", and No. 2015-201504, filed on Oct. 9, 2015, entitled "Test Piece Mounting Body, Transport Unit And Test Piece Analyzer", the entire contents of which are incorporated herein by reference.

BACKGROUND OF THE INVENTION

1. Field of the Invention

The invention relates to a test piece mounting body, transport unit, and test piece analyzer.

2. Description of the Related Art

A test piece that includes an elongated plate-like substrate, and a reagent layer formed on one surface of the substrate may be used when analyzing biological samples (particularly urine). When performing analysis using a test piece, a liquid sample such as urine makes contact with the reagent layer, and the presence and concentrations of the component of the samples are understood by the degree of coloration of the reagent layer.

There are analyzers provided with a transport unit to transport the test piece, and an imaging element to image the test piece that has been transported by the transport unit (for example, Japanese Laid-Open Patent Publication No. 2005-098937 and Japanese Laid-Open Patent Publication No. 2005-090969) that perform such analyses.

In the field of clinical examinations in recent years, examining a sample collected form a subject and immediately returning examination results, the so-called "Point of Care Test (POCT) has become popular. One example of this is the urine analyzer disclosed in Japanese Laid-Open Patent Publication No. 2005-098937.

This device immerses the test piece in the urine sample collected in a urine cup, and when the test piece is then placed on the test piece mounting body of the transport unit of the analyzer, the test piece is transported to a measuring unit inside the analyzer and imaged by the imaging element. The image obtained by the imaging element is analyzed to determine the concentration and pH and the like of the components (proteins, occult blood, sugar, specific gravity, white blood cells and the like) in the urine. The measured test piece is then automatically discarded from a disposal port of the side surface of the analyzer.

SUMMARY OF THE INVENTION

However, there are the following problems with the test piece mounting body used in the analyzer.

Since the test piece is immersed in a sample (urine sample) and mounted on the test piece mounting body of the transport unit, the sample (urine sample) adhered to the test piece mounting body is malodorous.

Alternatively, part of the sample (urine sample) remains on the test piece, and the test piece therefore may adhere to the test piece mounting body such that the test piece is not discarded from the disposal port provided in the side surface of the analyzer after analysis.

Alternatively, analyzers used in POCT examinations also are preferably sufficiently compact to be installed on a desktop. The urine analyzer disclosed in Japanese Laid-Open Patent Publication No. 2005-090969 is provided with a large, foldable imaging unit, and although compactness is realized by folding the imaging unit when the urine analyzer is stowed/transported, the compactness of the urine analyzer body is not disclosed in Japanese Laid-Open Patent Publication No. 2005-090969. A problem arises in making the urine analyzer more compact in that the test piece transport unit of the urine analyzer is connected to the test piece mounting body, and the test piece transport unit cannot be made more compact while ensuring the width of the test piece mounting body.

One aspect of the invention provides a test piece analyzer comprising: a transport unit with a transport device that transports a test piece; a drive part that drives the transport device; an imaging unit that captures an image of the test piece; and a casing that houses the transport unit, the imaging unit, and the drive part; wherein the transport unit is configured to be removable relative to the casing.

One aspect of the invention provides a test piece mounting body used in a test piece analyzer provided with a transport unit to transport a test piece from a first position to a second position, a drive part to drive the transport unit, and an imaging unit to image the test piece, the test piece mounting body including a bottom plate capable of mounting a test piece, wherein a plurality of bottom plate protrusions capable of supporting the test piece are formed on a first surface side of the bottom plate.

One aspect of the invention provides a transport unit to be used in a test piece analyzer including and imaging unit to image a test piece, provided with a transport device to transport a test piece from a first position to a second position that is the imaging position of the imaging unit, wherein the transport device includes a rotating body driven by the drive part, and an endless belt looped around the rotating body, and a plurality of test piece mounting bodies with mounted test pieces are attached independently to the endless belt.

According to one aspect of the invention, sample adhered to the transport unit can be easily washed because the transport unit is readily removable from the casing.

According to one aspect of the invention, the contact surface area between the bottom plate and the test piece can be reduced because bottom plate protrusions capable of supporting the test piece are formed on the bottom plate. The test piece therefore is unlikely to stick to the bottom plate even when liquid samples such as urine adhere to the bottom plate. Accordingly, obstruction of the operation of the analyzer due to test piece adhesion can be prevented from occurring.

According to one aspect of the invention, the transport unit can be smaller and the analyzer made more compact because the transport unit has a structure in which the test piece mounting bodies are independently attached to the endless belt.

BRIEF DESCRIPTION OF THE DRAWINGS

FIG. 6 is a perspective view showing the test piece mounting body of the analyzer of FIG. 1;

FIG. 7 is a perspective view showing the test piece mounting body of the analyzer of FIG. 1;

FIG. 8 is a frontal view showing the transport device and test piece mounting body of the analyzer of FIG. 1;

FIG. 9 is a perspective view showing the endless belt and test piece mounting body of the analyzer of FIG. 1;

DETAILED DESCRIPTION OF THE PREFERRED EMBODIMENTS

Figure 1:
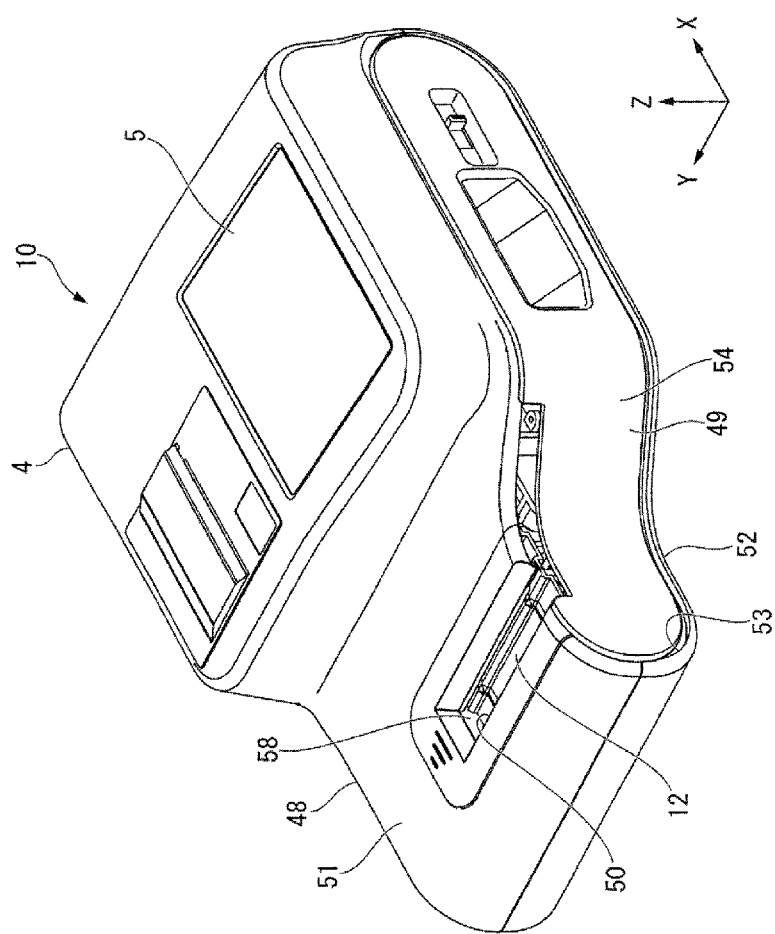
FIG. 1 is a perspective view showing an analyzer using the test piece mounting body of an embodiment of the invention.

The invention is described below based on the preferred embodiments and referring to the drawings.

Analyzer

FIG. 1 is a perspective view showing a test piece analyzer 10 (referred to below simply as "analyzer 10") using the test piece mounting body 12 of an embodiment of the invention.

Figure 2:
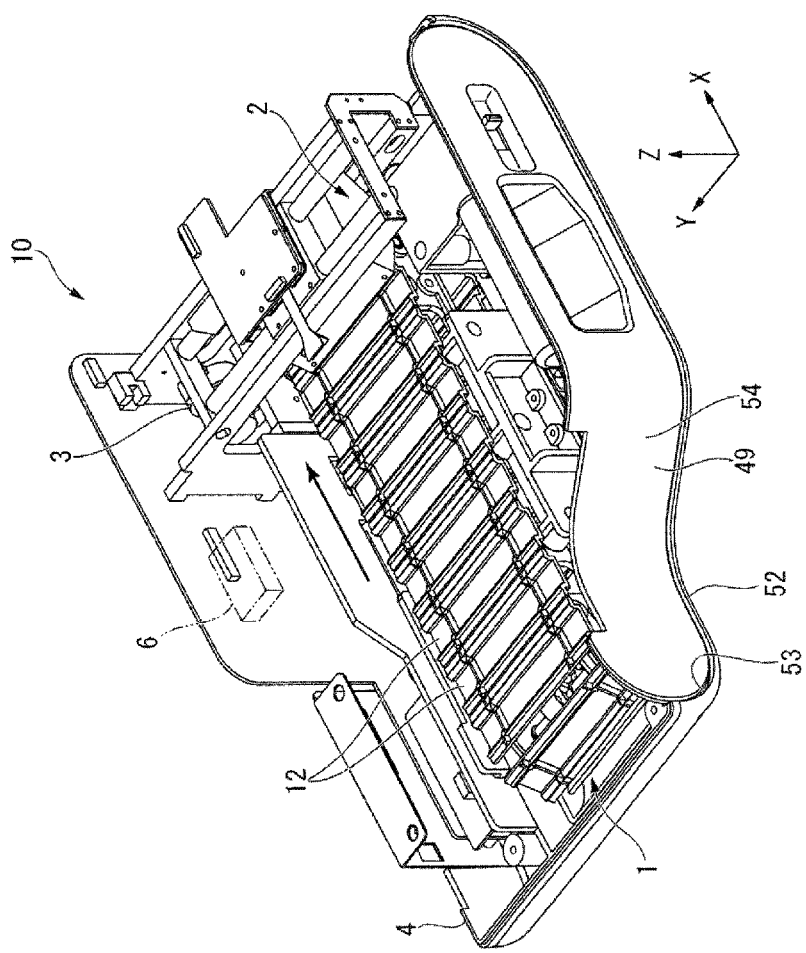
FIG. 2 is a perspective view showing the internal structure of the analyzer of FIG. 1.
Figure 3:
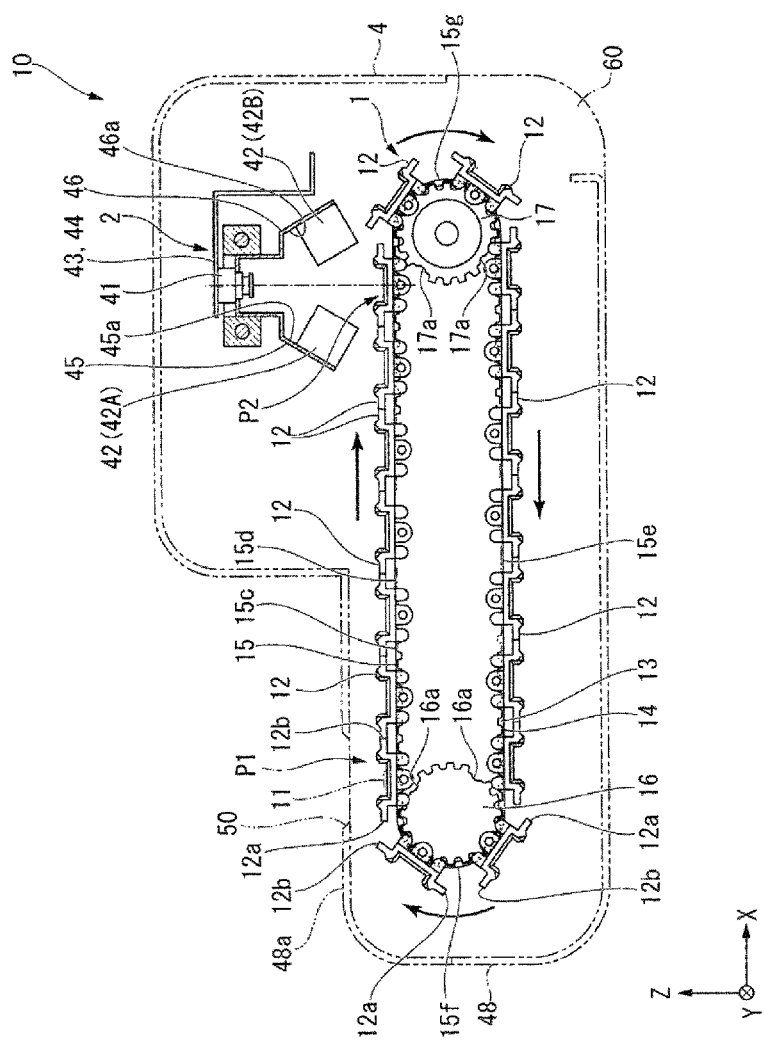
FIG. 3 is a side view schematically showing the internal structure of the analyzer of FIG. 1.

FIG. 2 is a perspective view showing the internal structure of the analyzer 10. FIG. 3 is a side view schematically showing the internal structure of the analyzer 10.

An XYZ orthogonal coordinate system is established in the following description. The X direction is the longitudinal direction of the endless belt that transports the test piece mounting bodies on which the test pieces are mounted, and is the lateral direction in FIG. 3. The Y direction is the width direction of the endless belt that transports the test piece mounting bodies on which the test pieces are mounted, and is the direction perpendicular to the drawing plane in FIG. 3. The Z direction is perpendicular to the X direction and the Y direction, and is the vertical direction in FIG. 3. Upward is also refers to the height direction.

The side surface of the test piece mounting body on which the test piece is mounted is designated the top side. The vertical direction matches the Z direction. The direction of travel of the test piece mounting body on which the test piece is mounted is referred to as forward, and the reverse direction is referred to as backward. Forward in FIG. 3 is in the right direction, and the backward is in the left direction. The front-to-back direction matches the X direction.

Figure 21:
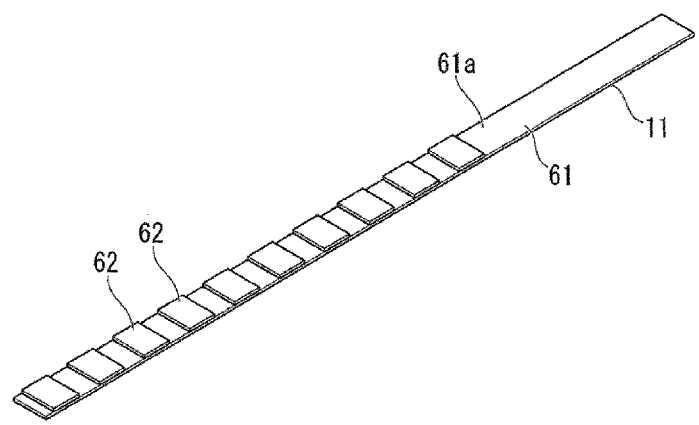
FIG. 21 is a perspective view showing an example of the test piece.

FIG. 21 is a perspective view showing a test piece 11, which is an example of the test piece. Test piece 11 has an elongated narrow plate-shaped substrate 61, and a plurality of reagent layers 62 formed on one surface 61a of the substrate 61. The reagent layers 62 attain a coloration in accordance with the presence and concentration of the components of a liquid sample when the analysis target liquid sample (urine or the like) comes into contact with the reagent layer 62.

As shown in FIG. 1 and FIG. 2, the analyzer 10 is provided with a transport unit 1 to mount and transport the test piece 11, an imaging unit 2 to image the test piece 11, a drive part 3 to drive the transport unit 1, a casing 4 to house these components, a display part 5, and a controller 6.

Figure 4:
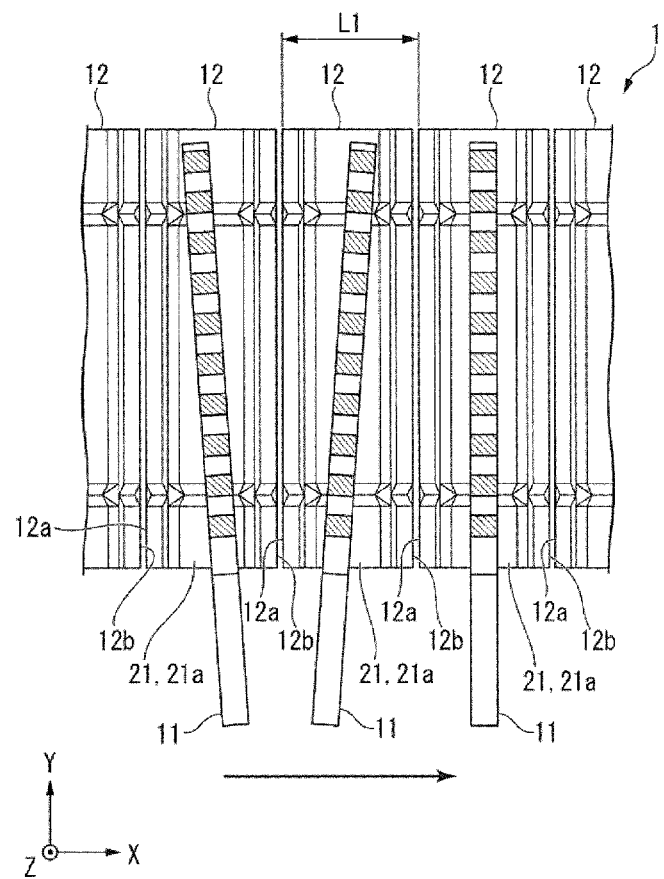
FIG. 4 is a plan view showing part of the transport unit of the analyzer of FIG. 1.
Figure 5:
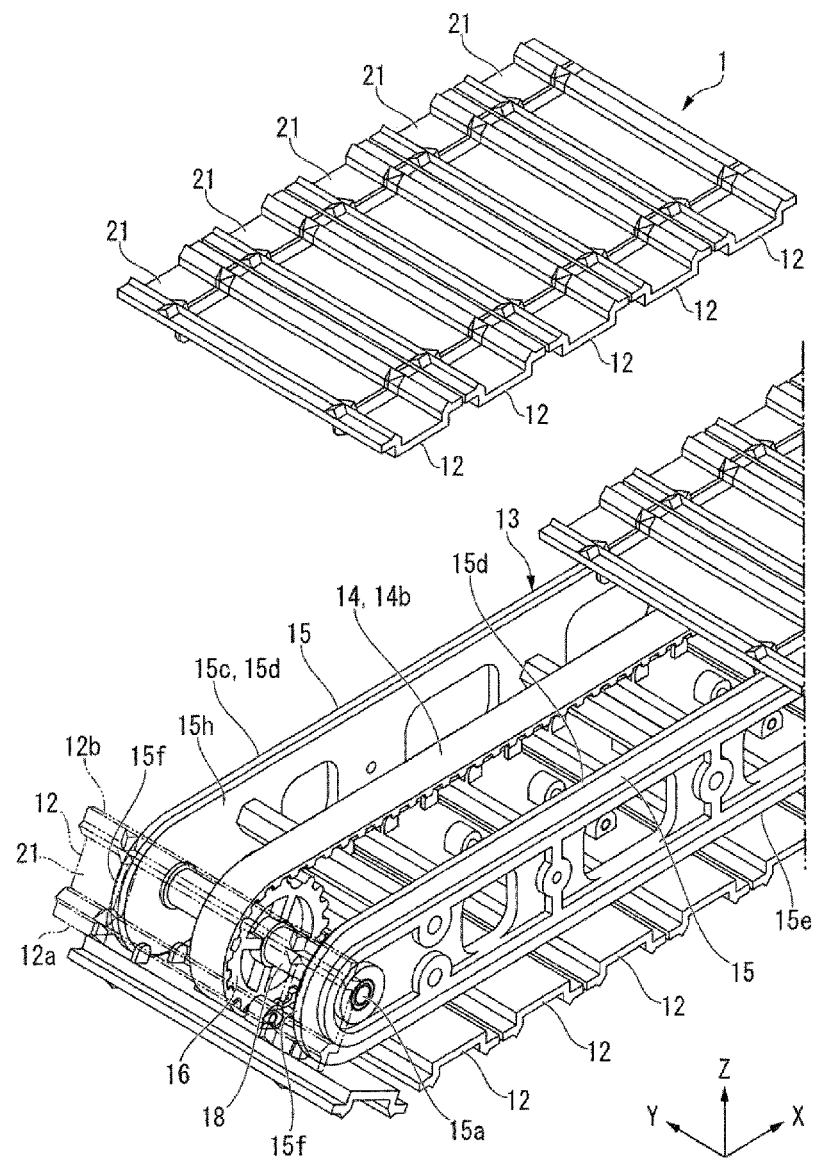
FIG. 5 is an exploded perspective view showing part of the transport unit of the analyzer of FIG. 1.

As shown in FIG. 3 through FIG. 5, the transport unit 1 has a plurality of test piece mounting bodies 12 on which to mount the test pieces 11, and a transport device 13 to transport the test piece mounting bodies 12.

Figure 12:
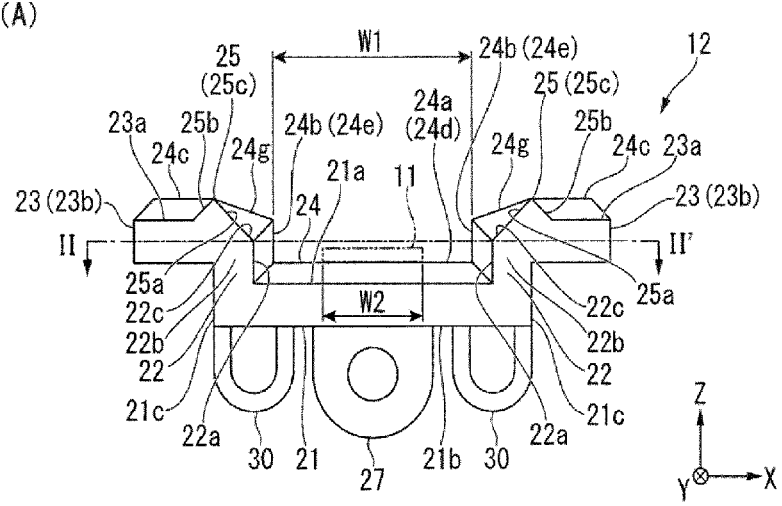
FIG. 12(A) is a side view of the test piece mounting body of the analyzer of FIG. 1.
FIG. 12(B) is a cross section view on the II-II' line shown in FIG. 12(A)
Figure 12:
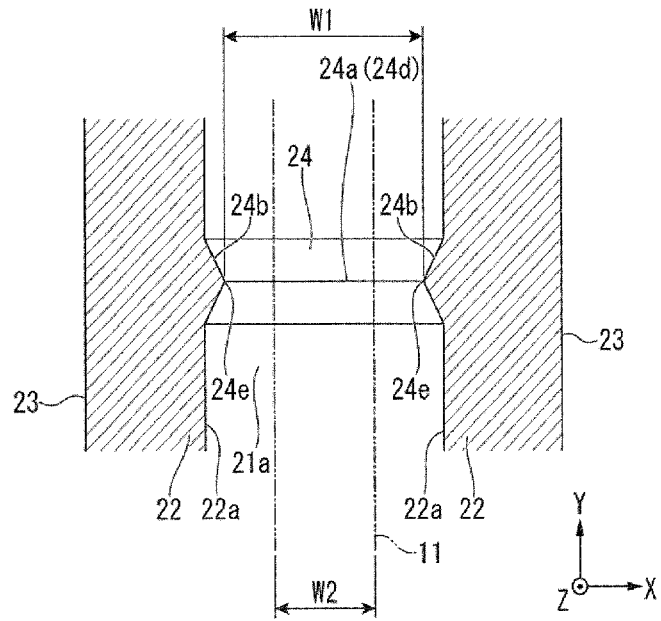

As shown in FIG. 6 and FIG. 12, the test piece mounting body 12, in plan view, is provided with a rectangular shaped bottom plate 21, side plates 22 and 22 respectively rising from the side edges 21c and 21c of the bottom plate 21, and extension plates 23 and 23 (blade part) which extend from the respective outside top edge 22b (protruding edge) of the side plates 22.

The top surface 21a of the bottom plate 21 is a first surface, and the bottom surface 21b is a second surface.

The side plates 22 protrude upward (the direction of the top surface 21 side, that is, the direction of the first surface side of the bottom plate 21) from the side edges 21c and 21c. The side plates 22 and 22 protrude along the YZ plane.

The top edge surfaces 22c (protruding edge surface) of the side plates 22 are inclined surfaces directed downward toward the internal side. Since the top edge surfaces 22c are inclined surfaces, light irradiating the test piece 11 from light sources 42 (refer to FIG. 3) of the imaging unit 2 is prevented from being blocked by the side plates 22. Note that the internal side in this case is a direction approaching the other side plate 22 viewed from one side plate 22.

The extension plate 23, for example, is provided for the purpose of regulating the spacing in the X direction of the body part (bottom plate 21 and side plates 22) of adjacent test piece mounting bodies 12. Disorder of the attitude of the test piece mounting body 12 can be prevented by providing the extension plate 23. For example, the test piece mounting body 12 can regulate the incline relative to the Y direction within the XY plane.

The extension direction of the extension plates 23 are the direction along the XY plane. Note that the outward extension direction of the one extension plate 23 is the direction away from the other extension plate 23 viewed from one extension plate 23.

Figure 11:
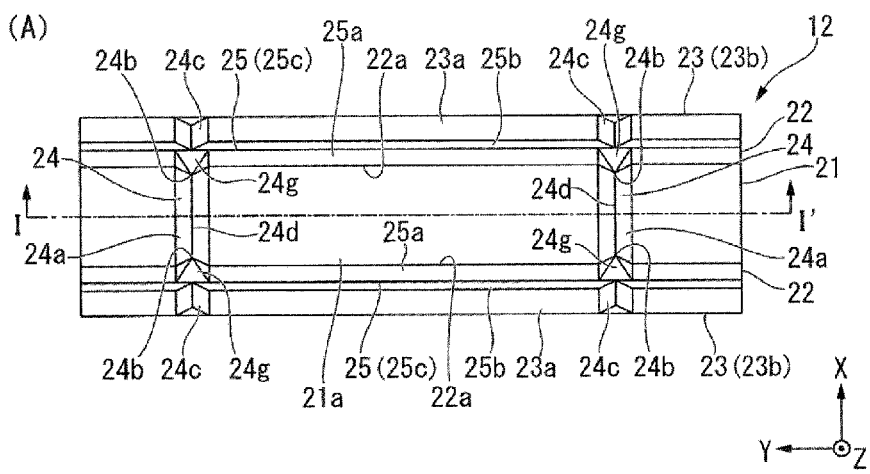
FIG. 11(A) is a plan view of the test piece mounting body of the analyzer of FIG. 1.
FIG. 11(B) is a cross section view on the I-I' line shown in FIG. 11(A)
FIG. 11(C) is an enlargement of FIG. 11(B)
Figure 11:
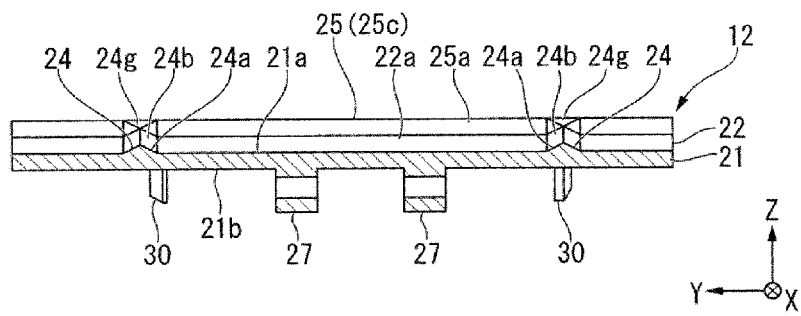
Figure 11:
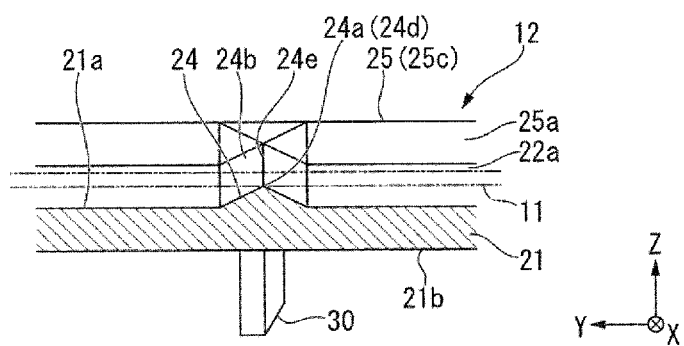

FIG. 11(A) is a plan view of the test piece mounting body 12. FIG. 11 (B) is a cross section view on the I-I' line shown in FIG. 11(A). FIG. 11(C) is an enlargement of FIG. 11(B). FIG. 12(A) is a side view (viewed from the Y direction) of the test piece mounting body 12. FIG. 12(B) is a cross section view on the II-II' line shown in FIG. 12(A). FIG. 13(A) is a plan view of the test piece mounting body 12. FIG. 13(B) is a cross section view on the III-III' line shown in FIG. 13(A). FIG. 13(C) is an enlargement of FIG. 13(B). FIG. 14(A) is a side view (viewed from the Y direction) of the test piece mounting body 12. FIG. 14 (B) is a cross section view on the IV-IV' line shown in FIG. 14(A).

As shown in FIG. 11 through FIG. 14, a pair of first rib-like protrusions 24 and a pair of second rib-like protrusions 25 are formed on the test piece mounting body 12.

As shown in FIG. 11 and FIG. 12, the pair of first rib-like protrusions 24 are formed in a space in the longitudinal direction (Y direction) of the test piece mounting body 12.

The first rib-like protrusions 24 have bottom plate protrusions 24a formed on the top surface 21a of the bottom plate 21, side plate protrusions 24b formed on the inside surface 22a of the side plate 22, intermediate protrusions 24g formed across the inside surface 25a of the second rib-like protrusions 25 from the top edge surface 22c of the side plate 22, and extension protrusions 24c formed on the top surface 23a of the extension plate 23.

As shown in FIG. 11, the bottom plate protrusion 24a is formed to project upward from the top surface 21a of the bottom plate 21. The bottom plate protrusions 24 extend across the entire width of the top surface 21a along the width direction (X direction) of the bottom plate 21. The protrusion height of the bottom plate protrusion 24a from the top surface 21a is preferably constant in the longitudinal direction (X direction).

The protrusion heights of the pair of bottom plate protrusions 24a are preferably equal to each other. In this way the test piece 11 can be supported parallel to the top surface 21a.

The bottom plate protrusions 24a are formed in the space in the longitudinal direction (Y direction) of the test piece mounting body 12. Note that the number of bottom plate protrusions 24a is not limited to two and may be three or more. Since the test piece 11 is supported at three or more points when three or more bottom plate protrusions 24a are formed, the test piece 11 is supported stably. Three or more bottom plate protrusions 24a also may be formed at equal intervals in the longitudinal direction (Y direction). In this case, since deflection of the test piece 11 in the longitudinal direction can be suppressed compared to when the test piece 11 is supported by two bottom plate protrusions 24a, the intensity of the light irradiating the test piece 11 is uniform in the longitudinal direction of the test piece mounting body 12. Therefore, reduction of analytic accuracy is prevented.

As shown in FIG. 11(C), the test piece 11 placed on the bottom plate 21 is supported on the bottom plate protrusions 24a since the bottom plate protrusions 24a are formed on the top surface 21a of the bottom plate 21. The test piece 11 is stably supported at two positions that are separated in the longitudinal direction because the pair of bottom plate protrusions 24a are formed in the space in the longitudinal direction of the test piece mounting body 12.

Since the test piece 11 is supported on the bottom plate protrusions 24a, the contact surface area between the bottom plate 21 and the test piece 11 can be reduced. The test piece 11 therefore is unlikely to stick to the bottom plate 21 even when liquid samples such as urine adhere to the bottom plate 21. Contamination between different liquid samples also can be prevented because the test piece 11 is prevented from touching the liquid sample on the bottom plate 21 even when liquid sample of a previous measurement remains on the bottom plate 21.

The cross sectional shape (the shape of the cross section perpendicular to the longitudinal direction of the bottom plate protrusion 24a) of the bottom plate protrusions 24a has a gradually narrowing width toward the protrusion direction (upward), for example, a triangular shape. The bottom plate protrusions 24a can support the test piece 11 on the peak 24d which is the uppermost part.

The bottom plate protrusions 24a have a smaller contact area with the test piece 11 because of the linear contact with the test piece 11 on the peak 24d (vertex). Thus, the test piece 11 is unlikely to stick to the bottom plate 21. Contamination between liquid samples also can be prevented.

As shown in FIG. 12, the side plate protrusion 24b is formed to protrude in an inward direction on the internal side surface 22a of the side plate 22. The side plate protrusion 24b extends across the total height of the internal side surface 22a along the width direction Z direction) of the side plate 22 from one end and the other end of the bottom plate protrusion 24a. The protrusion height of the side plate protrusion 24b from the internal side surface 22a is preferably constant in the longitudinal direction (Z direction). Note that the internal side direction in this case is the direction from one side plate 22 approaching the other side plate 22.

The side plate protrusion 24b is formed at a position that becomes contactable dependent on the mounting position of the test piece 11 supported on the bottom plate protrusion 24a.

The side plate protrusions 24b are formed in the space in the longitudinal direction (Y direction) of the test piece mounting body 12. Note that the number of side plate protrusions 24b (per one side plate 22) is not limited to two and also may be three or more.

The protrusion height of the side plate protrusion 24b is set so as to not obstruct the light irradiating the test piece 11 from the light sources 42 (refer to FIG. 3) of the imaging unit 2. The protrusion height of the side plate protrusion 24b is preferably as low as possible so as to not obstruct the irradiation light while supporting the test piece 11 on the test piece mounting body 12.

As shown in FIG. 12(B), the test piece 11 is arranged away from the internal side surface 22a even when the test piece 11 is near the side plate 22 because the side plate protrusions 24b are formed on the internal side surface 22a. Therefore, the contact surface area between the side plate 22 and the test piece 11 is reduced. The test piece 11 therefore is unlikely to stick to the side plate 22 even when liquid sample such as urine and the like adhere to the side plate 22.

Since the test piece 11 is arranged away from the internal side surface 22a of the side plate 22, the adverse effects and blurring of color of the reagent layers 62 are avoided in the image that might be caused by the shadow of the side plate 22 when the test piece 11 is imaged by the imaging unit 2 at the imaging position P2.

The cross sectional shape (the shape of the cross section perpendicular to the longitudinal direction of the side plate protrusion 24*b*) of the side plate protrusion 24*b* has a gradually narrowing width toward the protrusion direction (internal side direction), for example, a triangular shape. The side plate protrusion 24*b* can contact the test piece 11 at the peak 24*e* (vertex).

The contact surface area between the test piece 11 and the side plate protrusion 24*b* therefore can be smaller when the test piece 11 makes contact with the side plate protrusion 24*b*. Thus, the test piece 11 is more unlikely to stick to the side plate 22.

As shown in FIG. 14, the intermediate protrusion 24*g* is formed to protrude in a direction away from the surface on the internal side surface 25*a* of the second rib-like protrusion 25 and the top edge surface 22*c* of the side plate 22. The intermediate protrusion 24*g* is formed across the entire width of the internal side surface 25*a* and top edge surface 22*c* from the top edge of the side plate protrusion 24*b* to the peak 25*c* of the second rib-like protrusion 25.

The protrusion height of the intermediate protrusion 24*g* from the top edge surface 22*c* and the internal side surface 25*a* becomes lower the closer to the peak 25*c* of the second rib-like protrusion 25, and becomes zero at the top. As shown in FIG. 14(A), the height position (position in the Z direction) of the intermediate protrusion 24*g* can be the same position as the height position of the peak 25*c* of the second rib-like protrusion 25.

The intermediate protrusions 24*g* are formed in the space in the longitudinal direction (Y direction) of the test piece mounting body 12. Note that the number of intermediate protrusions 24*g* is not limited to two and also may be three or more.

Although the cross sectional shape (the shape of the cross section perpendicular to the longitudinal direction of the intermediate protrusion 24*g*) of the intermediate protrusion 24*g* is triangular at the bottom, the width mat be gradually trapezoidal (a trapezoid having a top surface 24*h*) toward the protrusion direction at positions between the bottom and top, as shown in FIG. 14(B).

Figure 13:
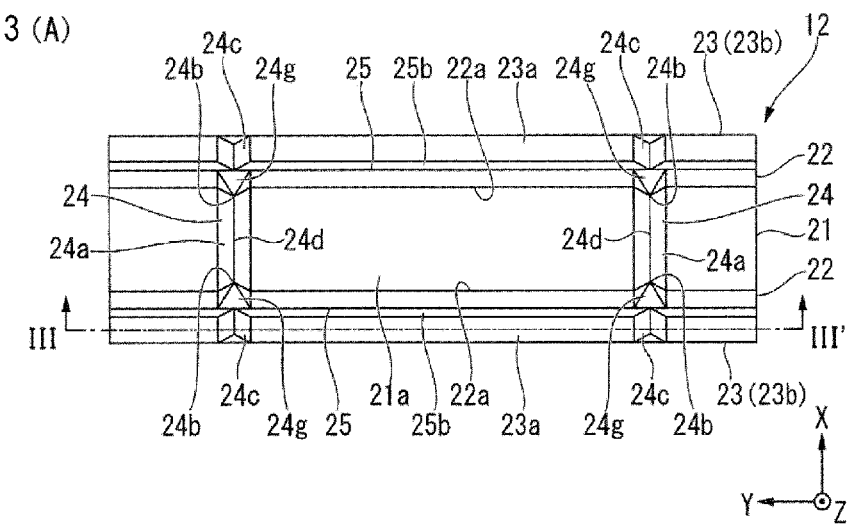
FIG. 13(A) is a plan view of the test piece mounting body of the analyzer of FIG. 1.
FIG. 13(B) is a cross section view on the III-III' line shown in FIG. 13(A)
FIG. 13(C) is an enlargement of FIG. 13(B)
Figure 13:
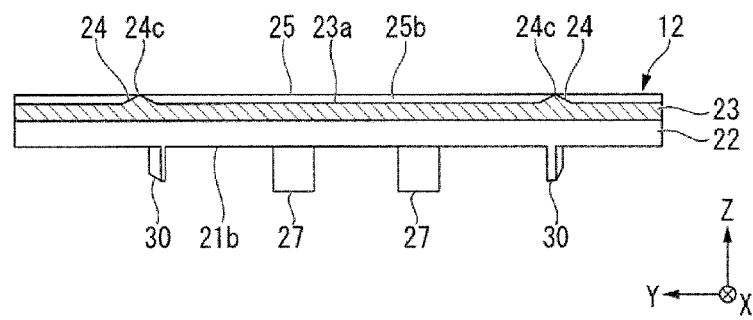
Figure 13:
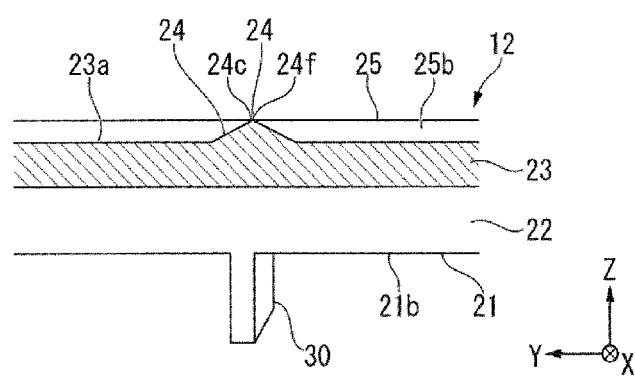
Figure 14:
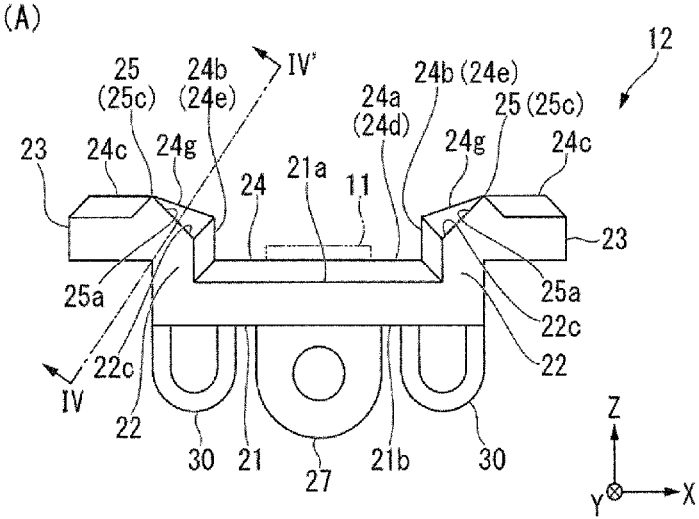
FIG. 14(A) is a side view of the test piece mounting body of the analyzer of FIG. 1.
FIG. 14(B) is a cross section view on the IV-IV' line shown in FIG. 14(A)
Figure 14:
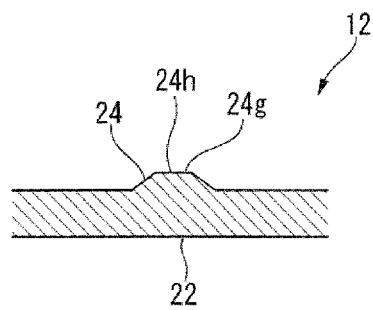

As shown in FIG. 13, the extension plate protrusion 24*c* is formed to project upward from the top surface 23*a* (the surface on the extension direction side of the side plate 22) of the extension plate 23. The extension plate protrusion 24*c*. The extension plate protrusion 24*c* extends from the outside surface 25*b* of the second rib-like protrusion 25, and reaches the outside edge 23*b* of the extension plate 23. The protrusion height of the extension plate protrusion 24*c* from the top surface 23*a* is preferably constant in the longitudinal direction (X direction).

As shown in FIG. 13(C), since the extension plate protrusions 24*c* are formed on the top surface 23*a* of the extension plate 23, the test piece 11 is supported by the extension plate protrusions 24*c* even when the test piece 11 is placed on the extension plate 23. The contact surface area between the test piece 11 and the extension plate 23 therefore can be smaller. Thus, the test piece 11 is unlikely to stick to the extension plate 23 and the test piece 11 can be readily discarded even when liquid sample such as urine adheres to the extension plate 23.

The extension plate protrusions 24*c* are formed in the space in the longitudinal direction (Y direction) of the test piece mounting body 12. Note that the number of extension plate protrusions 24*c* (per one extension plate 23) is not limited to two, and may be three or more.

The cross sectional shape (the shape of the cross section perpendicular to the longitudinal direction of the extension plate protrusion 24*c*) of the extension plate protrusions 24*c* has a gradually narrowing width toward the protrusion direction (upward), for example, a triangular shape. The contact surface area with the test piece 11 can be smaller since the extension plate protrusions 24*c* linearly contact test piece 11 at the peak 24*f* (vertex) even when the test piece 11 is placed on the extension plate 23. Thus, the test piece 11 is more unlikely to stick to the extension plate 23. The protrusion height of the extension plate protrusion 24*c* is preferably as low as possible to avoid obstructing the irradiation light.

The second rib-like protrusions 25 are respectively formed on the top surfaces 23*a* of the extension plates 23. The second rib-like protrusions 25 can be formed so as to reach the top edge surfaces 22*c* of the side plates 22. The internal side surface 25*a* of the second rib-like protrusion 25 can be made flush with the top edge surface 22*c*.

The second rib-like protrusions 25 are formed to protrude upward from the top surfaces 23*a* of the extension plates 23. The second rib-like protrusions 25 extend across the entire length of the top surface 23*a* along the longitudinal direction (Y direction) of the extension plate 23. The protrusion height of the second rib-like protrusion 25 from the top surface 23*a* is preferably constant in the longitudinal direction (Y direction).

The protrusion height of the second rib-like protrusion 225 is set so as to not obstruct the light irradiating the test piece 11 from the light sources 42 (refer to FIG. 3) of the imaging unit 2. The protrusion height of the second rib-like protrusion 25 is preferably as low as possible to avoid obstructing the irradiation light.

Since the second rib-like protrusions 25 are formed on the top surface 23*a* of the extension plate 23, the test piece 11 is supported by the second rib-like protrusions 25 even when the test piece 11 is placed on the extension plate 23. The contact surface area between the test piece 11 and the extension plate 23 therefore can be smaller. Thus, the test piece 11 is unlikely to stick to the extension plate 23 and the test piece 11 can be easily discarded even when liquid sample such as urine adheres to the extension plate 23.

The cross sectional shape (the shape of the cross section perpendicular to the longitudinal direction of the second rib-like protrusion 25) of the second rib-like protrusion 25 has a gradually narrowing width toward the protrusion direction (upward), for example, a triangular shape. The contact surface area with the test piece 11 can be smaller since the second rib-like protrusions 25 linearly contact the test piece 11 at the peak 25*c* (vertex) even when the test piece 11 is placed on the extension plate 23. Thus, the test piece 11 is more unlikely to stick to the extension plate 23.

The height position (position in the Z direction) of the vertex 25*c* of the second rib-like protrusion 25 can be constant across the entire length. The intensity of the light irradiating the test piece from the light sources 42 (refer to FIG. 3) of the imaging unit 2 therefore can be uniform in the length direction of the test piece mounting body 12. Thus, reduction of analysis accuracy can be prevented.

As shown in FIG. 12, the distance W1 (distance in the X direction) between the opposite side plate protrusions 24*b* of the side plates 22 is preferably greater than the width W2 (the dimension in the lateral direction of the test piece 11) of the test piece 11.

When the distance W1 is greater than the width W2 of the test piece 11, there are fewer limitations on the attitude of the test piece 11 and the position of the test piece 11 on the bottom plate 21. For example, the placement position of the test piece 11 may be a position to the side rather than the center in the width direction (X direction) of the bottom plate 21, and the test piece 11 also may be inclined relative to the longitudinal direction (Y direction) of the test piece mounting body 12 in plan view. The operation of placing the test piece 11 on the test piece mounting body 12 therefore can be easily performed. Costs also can be controlled since a device to line up the test piece 11 is unnecessary.

The width D=W2 of the test piece 11 is, for example, 4 to 6 mm, and the distance W1 is larger, for example, 5 to 12 mm.

The distance W1 preferably does not exceed double the width of the test piece 11. The operational error when placing the test piece 11 on the test piece mounting body 12 becomes unlikely when the distance W1 is double or less the width of the test piece 11.

Note that the distance W1 is the distance between the vertices 24e of the opposite side plate protrusions 24b. The distance W1 is the distance in the width direction (X direction) of the space within the test piece mounting body 12 where the test piece 11 can be placed within the internal space (the space on the top surface 21a side) formed by the bottom plate 21 and side plates 22. Note that in a test piece mounting body that is not configured with side plate protrusions, the distance in the width direction (X direction) of the space within the test piece mounting body where the test piece 11 can be placed is the distance between the internal surfaces of the pair of side plates.

As shown in FIG. 7 through FIG. 9, a pair of shaft support parts 27 are formed in the space in the longitudinal direction (Y direction) of the bottom plate 21 on the bottom surface 21b of the bottom plate 21.

As shown in FIG. 7, the shaft support parts 27 are semi-oval cross section protrusions extending in the longitudinal direction (Y direction) of the bottom plate 21, and insertion holes 27a are formed for the insertion of a support bar 28. The insertion holes 27a are formed through the shaft support parts 27 along the longitudinal direction (Y direction) of the bottom plate 21.

The spacing of the shaft support parts 27 preferably is the same as, or slightly larger than, the width of the endless belt 14. The endless belt 14 is arranged in the space 29 between the shaft support parts 27, as shown in FIG. 8 and FIG. 9.

As shown in FIG. 9, one end and the other end of the support shaft 28 are respectively inserted in the insertion holes 27a.

At least part of the support bar 28 is shaped to enter and be held by a holding recess 31 of the endless belt 14. The support bar 28 may be, for example, a circular cross section rod-like body.

As shown in FIG. 8 and FIG. 9, the test piece mounting body 12 is attached to the outside surface 14b side of the endless belt 14 by arranging the endless belt 14 in the space 29 between the shaft support parts 27, and fitting the support bar 28 in the insertion holes 27a while locking the support bar 28 in the holding recess 31.

The bottom side 21b of the test piece mounting body 12 attached to the endless belt 14 preferably is in a state of contact (or near contact) with the outside surface 14b of the endless belt 14. In this way the horizontal attitude of the top surface 21a of the bottom plate 21 is maintained since the test piece mounting body 12 positioned on the top side of the guide plate 15 is supported by the endless belt 14 across the entire width of the bottom surface 21b.

As shown in FIG. 7, at least one (and preferably both) side edges 21b1, of one and the other edge in the width direction (X direction) of the bottom surface 21b of the bottom plate 21, preferably is not fixedly attached to the endless belt 14.

Note that although the mounting structure configured by the shaft support part and supper bar can be established at two or more locations at different positions in the width direction of the bottom surface of the test piece mounting body, the mounting structure preferably is established at only one location of the bottom surface 21b of the test piece mounting body 12. According to this configuration, movement of the test piece mounting body 12 can be ensured sufficiently as necessary since the test piece mounting body 12 can be moved in rotation along the Y direction by the turning of the support bar 28 acting as a rotation shaft.

Therefore, when the endless belt 14 is in a curved state at the pulleys 16 and 17, the test piece mounting body 12 operates smoothly with the side edges 21b1 apart from the endless belt 14, and the force acting on the endless belt 14 can be reduced. The attitude of the test piece mounting body 12 also can be maintained horizontally when the endless belt 14 is in a linear state between the front pulley 16 and back pulley 17.

As shown in FIG. 7 through FIG. 9, a pair of positioning protrusions 30 (30A, 30A) are formed so as to protrude downward at a position nearer one end of the bottom plate 21 from the shaft support parts 27 on the bottom surface 21b of the bottom plate 21. The positioning protrusions 30 (30A, 30A) are formed side by side in the width direction (X direction) of the bottom plate 21.

A pair of positioning protrusions 30 (30B, 30B) are formed to protrude downward nearer the other edge of the bottom plate 21 from the shaft support parts 27. The pair of positioning protrusions 30 (30B, 30B) are formed side by side in the width direction (X direction) of the bottom plate 21.

The positioning protrusion 30 has a vertical half-length circular plate shape relative to the longitudinal direction (Y direction) of the bottom plate 21.

A plurality of test piece mounting bodies 12 are mounted on the endless belt 14 independently of each other. Therefore, one edge 12a of a test piece mounting body 12 and another edge 12b of an adjacent test piece mounting body 12 can be arranged in mutual proximity while maintaining mutual separation, for example, as shown in FIG. 3 through FIG. 5.

As shown in FIG. 3, when test piece mounting bodies 12 are at positions corresponding to the top edge 15d and bottom edge 15e of the guide plate 15, for example, one edge 12a of a first test piece mounting body 12 and another edge 12b of another test piece mounting body 12 adjacent to the first test piece mounting body 12 are in mutual proximity.

Conversely, when test piece mounting bodies 12 are at positions corresponding to the end edges 15g and 15g of the guide plate 15 and pulleys 16 and 17, one edge 12a of a first test piece mounting body 12 and another edge 12b of another test piece mounting body 12 adjacent to the first test piece mounting body 12 are widely separated.

When test piece mounting bodies 12 are at positions corresponding to end edges 15f and 15g of the guide plate 15 and pulleys 16 and 17, the separation distance increases from one edge 12a and the other edge 12b compared to when the positions correspond to the top edge 15d and bottom edge 15e.

A plurality of test piece mounting bodies 12 are mounted side by side in the longitudinal direction of the endless belt 14. In this way work efficiency is improved because a plurality of test pieces 11 are continuously provided for analysis.

As shown in FIG. 3 and FIG. 4, the plurality of test piece mounting bodies 12 preferably are mounted on the endless belt 14 so that the gap between adjacent test piece mounting bodies 12 is as small as possible. In this way a plurality of test pieces 11 can be provided for analysis in a short time, and work is performed efficiently.

As shown in FIG. 4, the placement pitch L1 of the test piece mounting bodies 12 aligned in the longitudinal direction of the endless belt 14 preferably is the same, or a slightly larger, distance as the width of the test piece mounting body 12. The placement pitch L1, for example, is a distance in the X direction between one edge 12a of a test piece mounting body 12 and one edge 12a of the adjacent test piece mounting body 12.

The color of the test piece mounting body 12 preferably is a dark color (black or the like). When the test piece mounting body 12 is a dark color, contrast is heightened between the test piece 11 and the test piece mounting body 12 and image processing reliability is improved when performing processes such as extraction of the image of the test piece 11 from the image obtained by the imaging unit 2.

Figure 10:
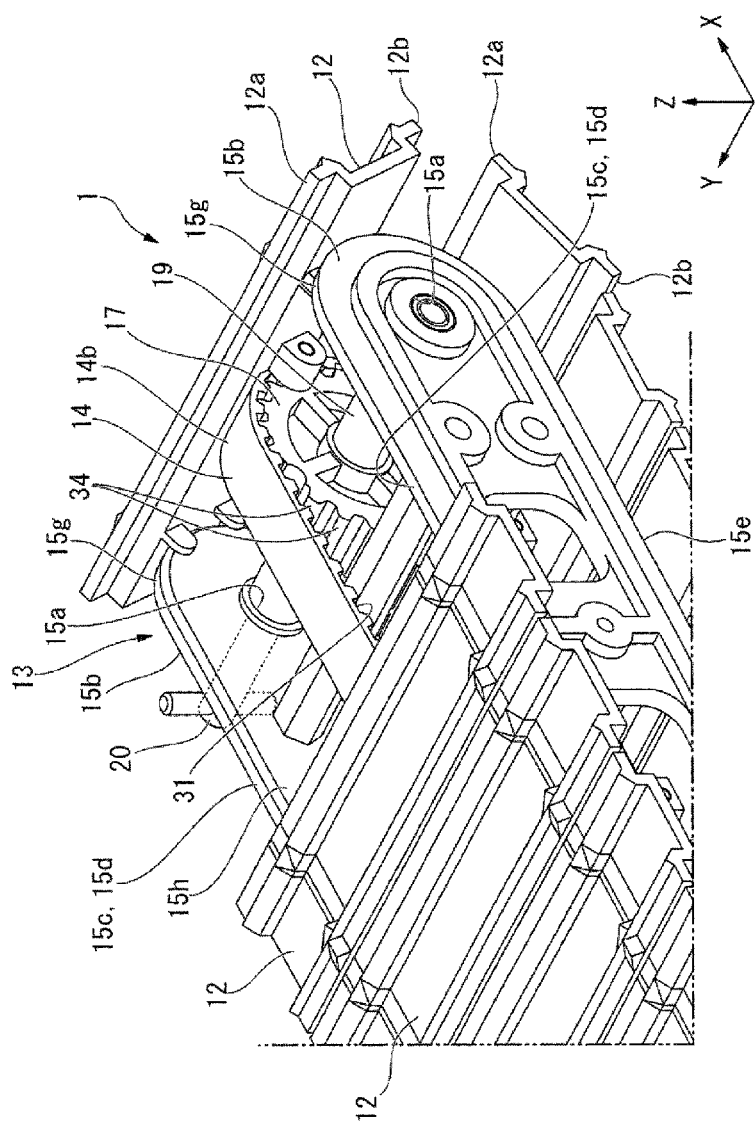
FIG. 10 is a perspective view showing part of the transport unit of the analyzer of FIG. 1.

As shown in FIG. 5 and FIG. 10, the transport device 13 is provided with the endless belt 14 on which the test piece mounting bodies 12 are mounted, guide plates 15 (guide parts) provided on one side and the other side of the endless belt 14, front pulley 16 and back pulley 17 (rotating bodies), front shaft 18 provided on the front pulley 16, and back shaft 19 provided on the back pulley 17.

The endless belt 14 is a band-like body (or belt-like body) formed in an annular shape. As shown in FIG. 9, the endless belt 14 preferably is a toothed belt since the belt must accurately transport the test piece mounting body 12, and to wash the removable transport unit 1.

For example, synthetic rubber, polyurethane and the like may be used as the toothed belt material. Stretching of the toothed belt can be suppressed by embedding a core wire such as steel wire, glass fiber, aramid fiber within the toothed belt.

As shown in FIG. 3, the front pulley 16 and the back pulley 17 are provided in a space in the front-to-back direction. A toothed pulley may be used as the front pulley 16 and back pulley 17. A toothed pulley as the front pulley 16 is referred to as the toothed front pulley 16, and a toothed pulley as the back pulley 17 is referred to as the toothed back pulley 17.

When using a toothed front pulley 16 and toothed back pulley 17, the teeth of the pulley will suitably mate with the teeth of the toothed belt (endless belt 14).

Notches 16a and 17a are formed intermittently to fend off the support bar 28 provided to attach the test piece mounting body 12 to the toothed belt, in addition to teeth to engage the teeth of the toothed belt (endless belt 14) on the outside peripheral edge of the toothed pulleys 16 and 17. The formation interval of the notches 16a and 17a, for example, are set to match the placement pitch L1 (refer to FIG. 4) of the test piece mounting body 12.

The number of teeth of the toothed belt and toothed pulleys 16 and 17 also are suitably selected so that the notches 16a and 17a of the outside peripheral edge of the toothed pulleys 16 and 17 normally match the position of the support bar 28 when the toothed belt circulates.

The shaft 18 extends from one side and the other side of the pulley 16 along the center axis of the pulley 16. The shaft 19 extends from one side and the other side of the pulley 17 along the center axis of the pulley 17. The front shaft 18 and the back shaft 19 are fixedly attached to the pulley 16 and 17, respectively.

The front shaft 18 and the back shaft 19 are supported on the guide plates 15 so as to be freely rotatable by part of one end and the other end of the shaft fit in the bearings 15a of the guide plates 15.

As shown FIG. 10, the extension shaft 20, which is part of one end of the back shaft 19, passes through the bearing 15a of the guide plate 15, and extends outward (Y direction) from the outside surface 15b of the guide plate 15.

As shown in FIG. 3, the guide plate 15 is an oval in plan view. The outside peripheral edge 15c of the guide plate 15, for example, has a linear top edge 15d and bottom edge 15e which are mutually parallel, a semicircular front end edge 15f formed at the front edge of the top edge 15d and bottom edge 15e, and a semicircular back end edge 15g formed at the back edge of the top edge 15d and bottom edge 15e. Note that the oval shape is a shape configured by a pair of parallel straight lines, and a curved convex shaped curve formed at one end and the other end of the straight lines.

As shown in FIG. 5 and FIG. 10, the pair of guide plates 15 are provided in a space from the endless belt 14 at one end and another end in the width direction (Y direction) of the endless belt 14.

As shown in FIG. 8, the interior surfaces 15h of the guide plates 15 are positioned in proximity to the outside surfaces 30a of the positioning protrusions 30 of the test piece mounting body 12 mounted on the endless belt 14. Therefore, the guide plates 15 regulate the movement in the longitudinal direction (Y direction) of the test piece mounting body 12, and can regulate positional dislocation of the test piece mounting body 12 from the track of the endless belt 14.

The top edge 15d of the guide plate 15 is positioned near the bottom surface 21b of the bottom plate 21 of the test piece mounting body 12 mounted on the endless belt 14. Therefore, the guide plates 15 regulate the tilting of the test piece mounting body 12, and can hold the attitude of the test piece mounting body 12 horizontally.

As shown in FIG. 5 and FIG. 10, bearings 15a fitted to freely rotate the leading end of the front shaft 18 and back shaft 19 are formed on one end and the other end of the guide plates 15.

As shown in FIG. 3, placement position P1 (first position) where the test piece 11 is placed on the test piece mounting body 12, and imaging position P2 (second position) where the test piece 11 is imaged by the imaging unit 2 are separated in the front-to-back direction. The placement position P1, for example, is a position near the front pulley 16. The imaging position P2, for example, is a position near the back pulley 17.

The transport unit 1 preferably can be cleaned as described later. It therefore is preferable that each part of the transport unit 1 is water resistant. The rotating shafts (shafts 18 and 19), support bar 28 for attaching the test piece mounting body 12 to the endless belt 14, and screws for attaching each component, for example, are constructed of stainless steel.

The guide plate 15, for example, is constructed of polyacetal resin with excellent sliding characteristics. Other components are constructed of suitably selected from among synthetic resins such as polyethylene terephthalate, polymethyl methacrylate, polystyrene, polycarbonate, and ABS.

As shown in FIG. 2 and FIG. 3, the imaging unit 2 is provided with an imaging element 41 to image the test piece 11, a pair of light sources 42 to irradiate the test piece 11, and a support body 43 to support the imaging element 41 and light sources 42.

As shown in FIG. 3, the support body 43 is provided with a top frame 44, front frame 45, and back frame 46 provided behind the front frame 45. The front frame 45 is inclined so as to descend toward the front. The back frame 46 is inclined so as to descend toward the back.

The imaging element 41 may be a two-dimensional RGB color image sensor. The imaging element 41 also may be two-dimensional monochrome image sensor combined with an RGB color filter.

The imaging element 41 is provided at the bottom surface of the top frame 44 of the support body 43.

For example, a light emitting diode (LED), incandescent lamp (halogen lamp, tungsten lamp and the like) fluorescent lamp, xenon lamp and the like may be used as the light source 42. Among these, LED is preferable.

The light sources 42 are respectively provided on the interior surface 45a of the front frame 45 and the interior surface 46a of the back frame 46 of the support body 43. Since the front frame 45 extends obliquely downward, the light source 42 (42A) provided on the front frame 45 irradiates light obliquely downward and backward. Since the back frame 46 extends obliquely downward, the light source 42 (42B) provided on the front frame 45 irradiates light obliquely downward and forward.

The position of the imaging unit 2 in the X direction is set to image the test piece 11 placed on the test piece mounting body 12 at the imaging position P2.

Specifically, the light sources 42 are installed as positions that allow irradiation of light from obliquely above and in front and obliquely above and behind the test piece mounting body 12 at imaging position P2. The imaging element 41 is installed above the test piece mounting body 12 at the imaging position P2 to image from above the test piece 11 placed on the test piece mounting body 12.

As shown in FIG. 2 and FIG. 10, the drive part 3 is, for example, a motor or the like, removably connected to the extension shaft 20 (refer to FIG. 10) of the shaft 19 of the transport device 13. The drive part 3 rotates the back pulley 17 by driving the rotation of the shaft 19, thereby circulating the endless belt 14.

It is preferable that the drive part 3 intermittently rotates the shaft 19 to intermittently move the test piece mounting body 12 mounted on the endless belt 14.

The connection between the drive part 3 and the extension shaft 20 can reliably transfer the rotational force of the drive part 3 to the extension shaft 20 when the drive part 3 and the extension shaft 20 are in the connected state, that is, the shape and mechanism is not particularly limited insofar as the components are freely detachable. The connector can release the drive part 3 and extension shaft 20. A well-known connecting device may be used as the connector.

Figure 15:
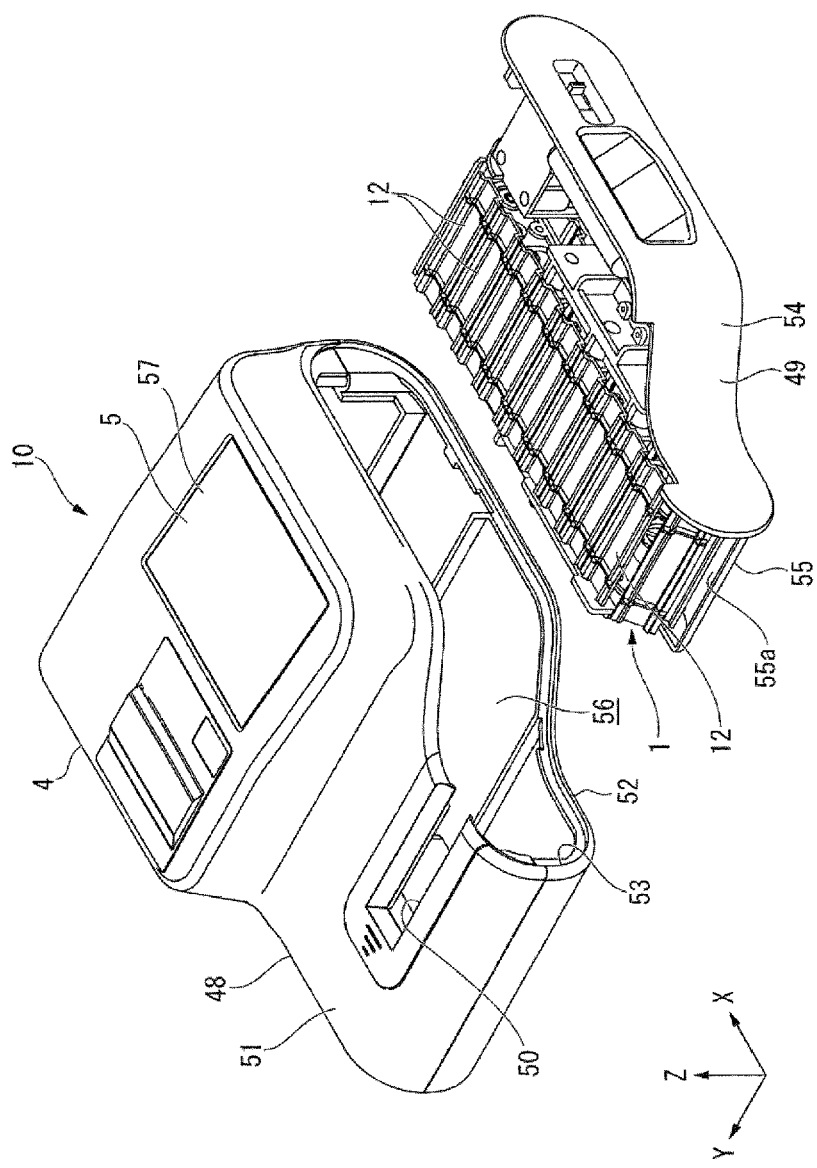
FIG. 15 is a perspective view showing the condition of the transport unit pulled out from the analyzer of FIG. 1.

As shown in FIG. 1 and FIG. 15, the casing 4 has an exterior part 48 (main casing part), and a pull-out part 49 that is separate from the exterior part 48.

Note that the structure including the imaging unit 2, drive part 3, and exterior part 48 is referred to as the "analyzer body".

The exterior part 48 can house the transport unit 1, top plate part 2, and drive part 3 in interior space 56 between the top plate 51 and the bottom plate 52. A pull-out port 53 for removing the transport unit 1 is formed on the side of the exterior part 48.

A placement port 50, which is an opening that exposes at least part of the test piece mounting body 12 at the placement position P1, is formed in the top plate of the exterior part 48. The placement port 50 is a slit-like opening formed along the Y direction.

The placement port 50 is formed to expose at least part of the top surface 21a (refer to FIG. 6) of the bottom plate 21 of the test piece mounting body 12 at the placement position P1.

The width (dimension in the X direction) of the placement port 50 preferably is larger than the width of the test piece 11, and preferably does not exceed the distance W1 shown in FIG. 6. The test piece 11 can be placed on the test piece mounting body 12 even when the direction of the test piece 11 is inclined relative to the Y direction in plan view, by making the width of the placement port 50 greater than the width of the test piece 11. The operation of placing the test piece 11 on the test piece mounting body 12 therefore can be easily performed.

An abutment wall 58 can be provided at a position allowing contact with the test piece 11 placed on the test piece mounting body 12 on the innermost part of the placement port 50. The abutment wall 58, for example, is formed along the XZ plane. Since the position in the Y direction of the test piece 11 can be regulated by the abutment wall 58, the test piece 11 can be prevented from dislocating from the position at which imaging is possible by the imaging unit 2.

As shown in FIG. 3, a discharge port 60 for discharging the test piece 11 that falls from the test piece mounting body 12 is formed in the exterior part 48. The discharge port 60 is an opening formed in the bottom part of the exterior part 48 of the casing 4.

As shown in FIG. 15, the pull-out part 49 has an exterior plate 54 that blocks substantially the entire pull-out port 53, and a support plate 55 that extends toward the interior of the exterior part 48 from the exterior plate 54.

The support plate 55 is formed along the XY plane, and supports the transport unit 1 installed on the top surface 55a, and is housed inside the exterior part 48 when the transport unit 1 is housed in the exterior part 48.

Since the pull-out part 49 is separate from the exterior part 48, the pull-out part 49 with the mounted transport unit 1 can be removed in the Y direction from the exterior part 48 if the transport unit 1 is disconnected from the drive part 3. The pull-out part 49 and the transport unit 1 can be freely taken out and put in relative to the exterior part 48, and the transport unit 1 and support plate 55 also can be rehoused in the exterior part 48.

The pull-out part 49 preferably is configured be detachably connected to the transport unit 1 through a connector (connecting means) such as a mounting clip 70a (refer to FIG. 22 and FIG. 24) which will be described later. It is possible to remove the transport unit 1 from the pull-out part 49 for washing via this configuration.

As shown in FIG. 1, the display part 5 can display operation guides and/or analysis results of the test piece.

The controller 6 can control the data processing of captured images and the operation of the device.

For example, the controller 6 can perform processing such as extracting the image of the test piece 11 from the image data obtained by the imaging unit 2.

The controller 6 also can batch control the operation of the analyzer 1. For example, the controller 6 can control the drive part 3 to drive the transport unit 1. The controller 6 also can control turning ON and OFF the light sources 42 of the imaging unit 2, and can operate the imaging element 41 to image the test piece 11.

The controller 6 can analyze the liquid sample by calculating the presence and concentration of components of the liquid sample from the degree of coloration of the reagent layer 62 (refer to FIG. 21) of the test piece 11 in contact with the liquid sample based on the image obtained by the imaging element 41.

Analyzer Use Method

The method of using the analyzer 10 is described below.

As shown in FIG. 3, the analyzer 10 is arranged so that the top surface 21a of the bottom plate 21 of the test piece mounting body 12 positioned on the top side of the guide plates 15 is horizontal.

The test piece 11 is placed on the bottom plate 21 of the test piece mounting body 12at the placement position P1, the extension shaft 20 is rotated around the axis by the drive part 3, and the back pulley 17 is rotated around the axis. The rotation direction of the back pulley 17 is the clockwise direction as indicated by the arrow in FIG. 3. The test piece 11 is placed with the reagent layer 62 (refer to FIG. 21) facing upward.

The drive part 3 is preferably drives intermittently. In this way the operation of moving the test piece mounting body 12 with mounted test piece 11 a fixed distance backward then temporarily stopped can be repeated since the back pulley 17 and endless belt 14 are driven intermittently. The moving distance of the endless belt 14 in one operation preferably is equal to the placement pitch L1 (refer to FIG. 4) of the test piece mounting body 12.

The endless belt 14 preferably travels so that the test piece mounting body 12 is stopped at the placement position P1.

As shown in FIG. 10, since the locking projections 34 of the back pulley 17 can lock to the holding recesses 31 of the endless belt 14, the endless belt 14 circulates in the clockwise direction in FIG. 3 in conjunction with the rotation of the back pulley 17.

As shown in FIG. 9, the test piece mounting body 12 circulates in conjunction with the circulation of the endless belt 14 because the support bar 28 provided on the test piece mounting body 12 can lock to the holding recesses 31 of the endless belt 14.

As shown in FIG. 3, the test piece mounting body 12 positioned on the top side of the transport device 13, that is, above the top edges 15d of the guide plates 15, moves backward (clockwise in FIG. 3) in conjunction with the travel of the rotation of the endless belt 14.

When the test piece mounting body 12 with mounted test piece 11 reaches the imaging position P2, the test piece 11 on the test piece mounting body 12 is sufficiently illuminated because light is irradiated on the test piece mounting body 12 obliquely from above and front and above and behind by the light sources 42 of the imaging unit 2. In this state the test piece 11 is imaged by the imaging element 41.

The endless belt 14 preferably travels so that the test piece mounting body 12 is stopped at the imaging position P2.

The time for the test piece mounting body to reach the imaging position P2 from the placement position P1 is set so that the components of the liquid sample and the reagent layer 62 of the test piece 11 react neither excessively nor insufficiently, so that the reagent layer is suitably colored.

The controller 6 can determine the presence and concentration of components of the liquid sample by calculation from the degree of coloration of the reagent layer 62 (refer to FIG. 21) of the test piece 11 in contact with the liquid sample based on the image obtained by the imaging element 41. In this way analysis results of the liquid sample are obtained.

As shown in FIG. 1, the analysis results preferably are displayed on the display part 5.

When the endless belt 14 circulates again and the test piece mounting body 12 with mounted test piece 11 reaches the back end edge 15g, the bottom plate 21 is inclined relative to the horizontal plane. In this way the test piece 11 falls from the test piece mounting body 12.

As shown in FIG. 3, the test piece 11 that has fallen from the test piece mounting body 12 is discharged through the discharge port 60 to the outside, and discarded as a used test piece 11.

As shown in FIG. 15, after measurements are completed, the pull-out part 49 and transport unit 1 are removed from the exterior part 48, and the transport unit 1 can be washed with wash water or the like. In this way fouling material can be washed off to clean the test piece mounting body 12 even when liquid sample has adhered to the test piece mounting body 12 during measurement. The pull-out part 49 and transport unit 1 are configured to be pulled out from the exterior part 48 releasing the extension shaft 20 of the transport unit and drive part 3 of the analyzer main body by operating the lever provided on one side of the pull-out part 49.

The clean transport unit 1 can be returned into the exterior part 48 by reversing the previously described pull out operation.

Figure 22:
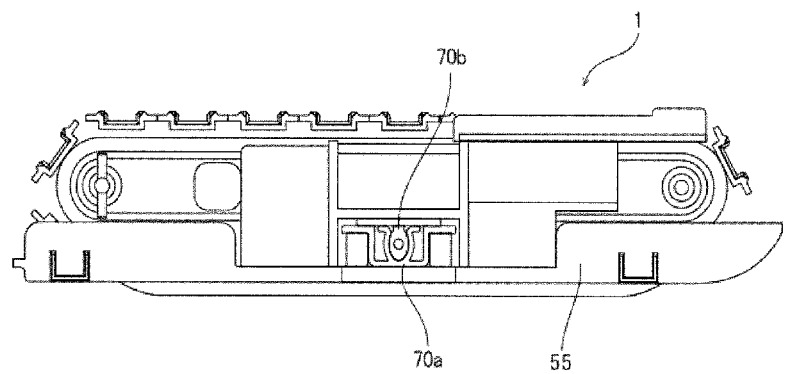
FIG. 22 is a side view showing the pull-out part and transport unit pulled out from the analyzer body.
Figure 24:
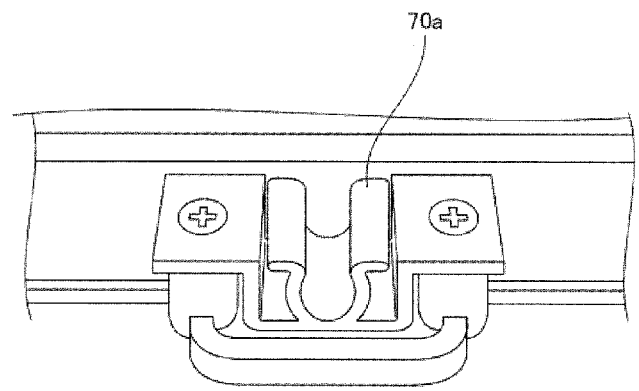
FIG. 24 is a perspective view showing the mounting clip (female connector part) for coupling the transport unit and pull-out part.
Figure 25:
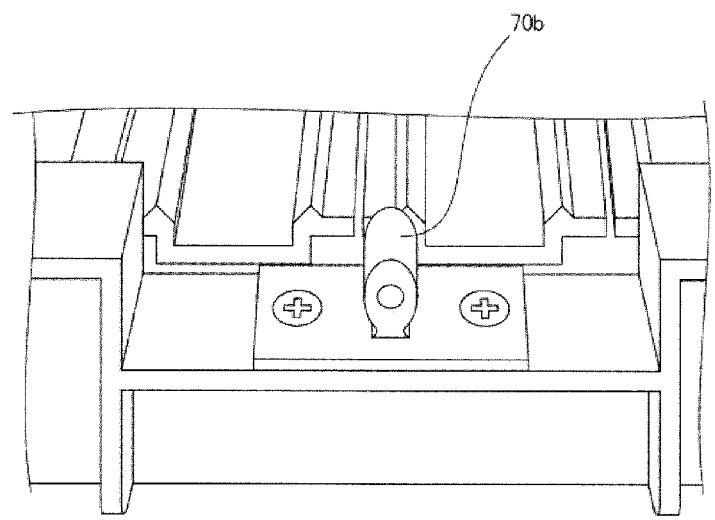
FIG. 25 is a perspective view showing the mounting clip (male connector part) for coupling the transport unit and pull-out part.

FIG. 22 is a side view showing the pull-out part 49 and transport unit 1 pulled out from the exterior part 48. A mounting clip 70a (female connecting part) shown in FIG. 24 is provided on the support plate part of the pull-out part 49, a mounting clip 70b male connecting part) shown in FIG. 25 is provided on the transport unit, and the mounting part 70a (female connecting part) and the mounting clip 70b (male connecting part) can be connected together. Although the mounting clips 70a and 70b are configured to be fitted together, the transport unit 1 can be detached from the pull-out part 49 through the mounting clips 70a and 70b since the mounting clips 70a and 70b are formed as flexible members.

Figure 23:
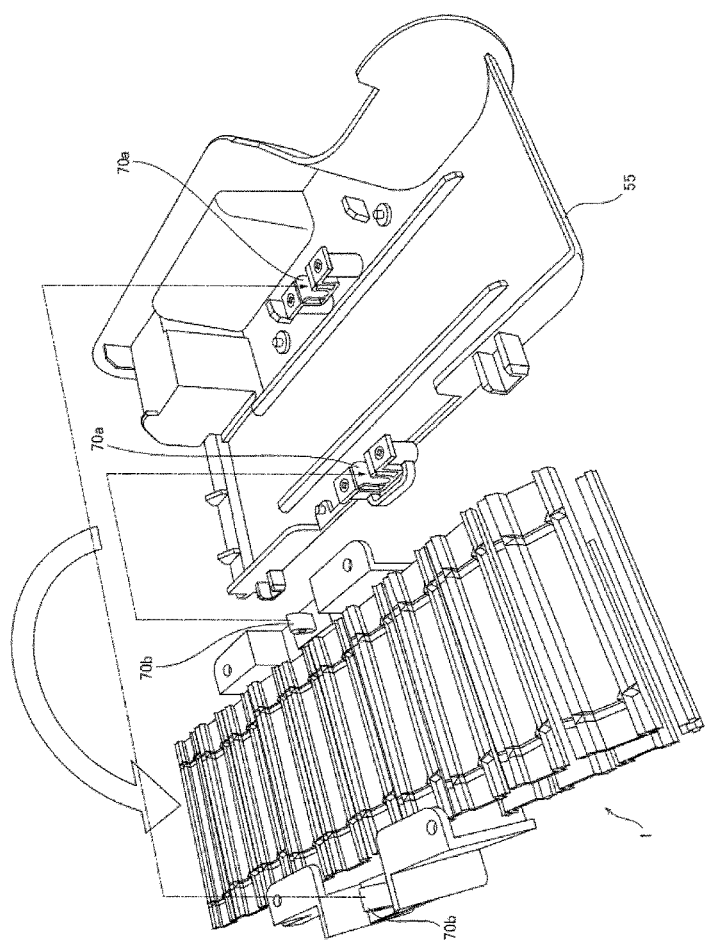
FIG. 23 is a perspective view showing the transport unit removed from the pull-out part.

FIG. 23 is a perspective view showing the transport unit 1 removed from the support plate 55 of the pull-out part 49. Although the pair of mounting clips 70b (male connecting parts) of the transport unit 1 are connected to the pair of mounting clips 70a (female connecting parts) provided on the support plate 55 before removing the transport unit 1, the transport unit 1 can be removed by grasping the transport unit 1 and pulling the transport unit 1 from the support plate 55 and to remove the mounting clips 70b from the mounting clips 70a.

Since the test piece mounting body 12 has the bottom plate protrusions 24a on the top surface 21a of the bottom plate 21, the test piece 11 is supported on the bottom plate protrusions 24a. The contact area between the bottom plate 21 and the test piece 11 therefore can be reduced. The test piece 11 therefore is unlikely to stick to the bottom plate 21 even when liquid samples such as urine adhere to the bottom plate 21.

Accordingly, obstruction of the operation of the analyzer 10 due to test piece adhesion can be prevented from occurring before it happens.

The transport unit 1 has a structure to mount the test piece mounting bodies 12 independently of one another on the endless belt 14. The front pulley 16 and back pulley 17 therefore can be smaller in diameter compared to a transport unit with a structure that mutually linked adjacent test piece mounting bodies together. Thus, the length (size in the X direction) and height (size in the Z direction) of the transport unit 1 can be smaller, and the analyzer 10 made more compact.

The smaller diameter of the pulleys 16 and 17 is possible because the test piece mounting bodies are not linked to one another and are independently mounted on the endless belt 14.

As shown in FIGS. 3 through 5, and FIG. 10, one edge 12*a* of a first test piece mounting body 12 and another edge 12*b* of another test piece mounting body 12 adjacent to the first mounting body 12 can be positioned spaced apart because the test piece mounting bodies 12 are not linked to one another in the analyzer 10. Therefore, the test piece mounting body 12 can move along the pulleys 16 and 17 unrelated to the width dimension of the test piece mounting body 12 even when the pulleys 16 and 17 have small diameters.

Conversely, in a structure in which the test piece mounting bodies are linked to one another, the test piece mounting bodies have difficulty moving along the pulleys when the pulleys have a small diameter.

Since the mounting structure configured by the shaft support part 27 and support bar 28 are provided only at one location on the bottom surface 21*b* of the test piece mounting body 12, the test piece mounting body 12 operates smoothly when the side edges 121*b*1 are in a state apart from the endless belt 14 when the endless belt 14 is in a curved state at the pulleys 16 and 17, and can be held in a horizontal attitude when the endless belt 14 is in a straight line between the front pulley 16 and back pulley 17.

Since there is little restriction of the width dimension of the test piece mounting body 12 in the analyzer 10, the width dimension of the test piece mounting body 12 can be sufficiently large. The operation of placing the test piece 11 on the test piece mounting body 12 can be easily performed by increasing the width dimension of the test piece mounting body 12.

Accordingly, the analyzer 10 can be made more compact without reducing the operability.

Since the transport unit 1 is freely put in and taken out of the exterior part 48 in the analyzer 10, the transport unit 1 can be removed from the exterior part 48 and washed after use.

Liquid sample adhered to the test piece 11 adhering to and becoming residue on the test piece mounting body 12 is not hygienically desirable.

Since the transport unit 1 can be easily washed, sanitation is not a problem in the analyzer 10.

As has been described to this point, the rotating bodies can have a smaller diameter by mounting the test piece mounting bodies independently of one another on the endless belt in the embodiment compared to transport units having a structure in which adjacent test piece mounting bodies are linked to each other. Therefore, the test piece transport unit can be made more compact than conventionally by reducing the length and height of the transport unit while ensuring the width of the test piece mounting body.

The entire transport unit also is removable from the analyzer body by releasing the drive part of the analyzer body and the shaft provided on the rotating body of the transport unit. Although urine sample adhered to the test piece mounting body is a noxious problem in urine analyzers, an operator can easily perform maintenance such as washing by removing the transport unit, handling is made easy by making the transport unit compact, and maintenance characteristics are greatly improved.

To make the transport unit removable, an opening for removal must be provided in the analyzer body, and sufficient space must be provided within the analyzer so as to not interfere with other parts during removal, and the apparatus body is easily enlarged. According to the embodiment, however, a smaller opening is provided in the analyzer body by making the transport unit smaller, and since the internal space in the analyzer needed for removal can be smaller, the apparatus body can be more compact with the advantage of removal.

The invention is not limited to the embodiment and may be suitably modified without departing from the scope of the invention.

As shown in FIG. 11 and beyond, the cross section shape of the first rib-like protrusion 24 and second rib-like protrusion 25 are described by way of example as triangular with gradually narrowing width in the protrusion direction, the cross section shape of the first rib-like protrusion 24 and second rib-like protrusion 25 are not specifically limited. FIG. 16 through FIG. 20 show modification of the first rib-like protrusion.

Figure 16:
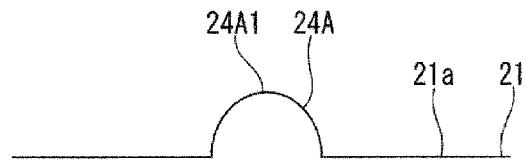
FIG. 16 shows the cross sectional shape of a first modification of a rib-like protrusion of the analyzer of FIG. 1.

The first rib-like protrusion 24A shown in FIG. 16 is a first modification of the first rib-like protrusion 24. The first rib-like protrusion 24A has a semicircular shape cross section, and is formed to protrude upward from the top surface 21*a* of the bottom plate 21. The first rib-like protrusion 24A can support the test piece 11 on the peak 24A1 which is the uppermost part.

Figure 17:
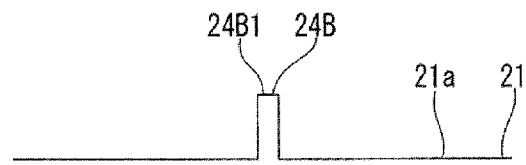
FIG. 17 shows the cross sectional shape of a second modification of a rib-like protrusion of the analyzer of FIG. 1.

The first rib-like protrusion 24B shown in FIG. 17 is a second modification of the first rib-like protrusion 24. The first rib-like protrusion 24B has a rectangular shape cross section, and is formed to protrude upward from the top surface 21*a* of the bottom plate 21. The first rib-like protrusion 24B can support the test piece 11 on the peak 24B 1 (top surface) which is the uppermost part.

Figure 18:
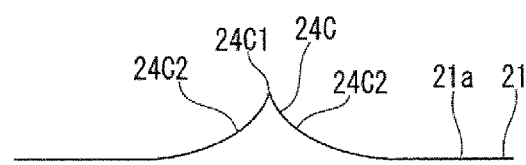
FIG. 18 shows the cross sectional shape of a third modification of a rib-like protrusion of the analyzer of FIG. 1.

The first rib-like protrusion 24C shown in FIG. 18 is a third modification of the first rib-like protrusion 24. The first rib-like protrusion 24C has a side surface 24C2 that is a concave curved surface having a substantially elliptical arc-shaped cross section. The side surface 24C2 is inclined so as to rise toward the peak 24C1 from the exterior side edge. The first rib-like protrusions 24C is formed to protrude upward from the top surface 21*a* of the bottom plate 21, with a shape of gradually narrowing width to a sharp peak 24C1 toward the protrusion direction (upward). The first rib-like protrusion 24C can support the test piece 11 on the peak 24C1 which is the uppermost part.

Figure 19:
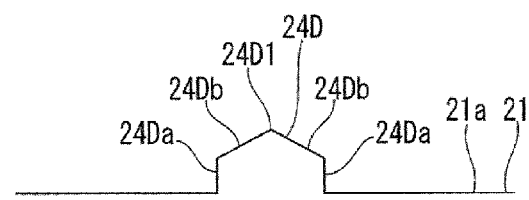
FIG. 19 shows the cross sectional shape of a fourth modification of a rib-like protrusion of the analyzer of FIG. 1.

The first rib-like protrusion 24D shown in FIG. 19 is a fourth modification of the first rib-like protrusion 24. The first rib-like protrusion 24D is formed to protrude upward from the top surface 21*a* of the bottom plate 21, with a shape that has a bottom side surface 24D*a* perpendicular to the top surface 21*a* of the bottom plate 21, and a top side surface 24D*b* inclined to rise toward the peak 24D1 from the exterior side edge. The first rib-like protrusion 24D can support the test piece 11 on the peak 24D1 which is the uppermost part.

Figure 20:
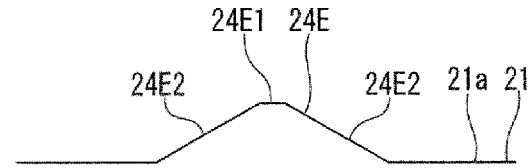
FIG. 20 shows the cross sectional shape of a fifth modification of a rib-like protrusion of the analyzer of FIG. 1.

The first rib-like protrusion 24E shown in FIG. 20 is a fifth modification of the first rib-like protrusion 24. The first rib-like protrusion 24E is formed to protrude upward from the top surface 21*a* of the bottom plate 21, with a shape that has a side surface 24E2 inclined so as to rise toward the peak 24E1 from the exterior side edge, and a peak 24E1 parallel to the top surface 21*a*. The first rib-like protrusion 24E can support the test piece 11 on the peak 24E1 which is the uppermost part.

The shapes of the first rib-like protrusions 24 shown in FIG. 16 through FIG. 20 also are applicable to the second rib-like protrusion 25.

As shown in FIG. 11 and beyond, although the extension direction of the bottom plate protrusions 24*a* is perpendicular to the longitudinal direction of the bottom plate 21 in the test piece mounting body 12, the extension direction of the bottom plate protrusions is not limited to this direction if the direction intersects the longitudinal direction of the bottom plate 21. This direction, for example, may be a direction inclined at an angle of more than 0 degrees and less than 90 degrees relative to the Y direction within the XY plane.

Although the extension direction of the side plate protrusion 24b is perpendicular to the longitudinal direction (Y direction) of the side plate 22, the extension direction of the side plate protrusion is not limited to this direction if the direction intersects the longitudinal direction of the side plate 22. This direction, for example, may be a direction inclined at an angle of more than 0 degrees and less than 90 degrees relative to the Y direction within the YZ plane.

The extension direction of the intermediate protrusion is not limited to the examples shown in the drawings, if the direction intersects the Y direction in the plan view. This direction, for example, may be a direction inclined at an angle of more than 0 degrees and less than 90 degrees relative to the Y direction.

Although the extension direction of the extension plate protrusion 24c is perpendicular to the longitudinal direction (Y direction) of the extension plate 23, the extension direction of the extension plate protrusion is not limited to this direction if the direction intersects the longitudinal direction of the extension plate 23. This direction, for example, may be a direction inclined at an angle of more than 0 degrees and less than 90 degrees relative to the Y direction within the XY plane.

Although the extension direction of the second rib-like protrusion 25 is perpendicular to the width direction (X direction) of the extension plate 23, the extension direction of the second rib-like protrusion is not limited to this direction if the direction intersects the width direction of the extension plate 23. This direction, for example, may be a direction inclined at an angle of more than 0 degrees and less than 90 degrees relative to the X direction within the XY plane.

The extension direction of the bottom plate protrusions 24a is not limited to a direction intersecting the longitudinal direction of the bottom plate 21, and also may extend in the longitudinal direction of the bottom plate 21. In this case, the plurality of protrusions also may extend parallel to each other in the longitudinal direction of the bottom plate 21.

As shown in FIG. 11 and beyond, although the bottom plate protrusion 24a is formed across the entire width of the top surface 21a in the test piece mounting body 12, one or both of the one end or the other end of the bottom plate protrusion also need not reach the side edge of the top surface 21a of the bottom plate 21.

Although the side plate protrusion 24b is formed across the entire height of the interior side surface 22a, one or both bottom end and top end of the side plate protrusion also need not reach the bottom edge and top edge of the interior side surface 22a, respectively.

Although the intermediate protrusion 24g is formed across the entire width of the top edge surface 22c and interior side surface 25a, the bottom end of the intermediate protrusion need not reach the bottom edge of the top edge surface 22c, and the top end of the intermediate protrusion need not reach the top edge of the interior side surface 25a.

Although the extension plate protrusion 24c is formed substantially across the entire width of the top surface 23a, one end of the extension plate protrusion need not reach the exterior side surface 25b, and the other end of the extension plate protrusion need not reach the exterior side edge 23b of the extension plate 23.

Although the test piece mounting body 12 shown in FIG. 11 and beyond has first rib-like protrusions 24 and second rib-like protrusions 25, the test piece mounting body also may be configured without the second rib-like protrusion in the invention.

Although, in the test piece mounting body 12, the first rib-like protrusion 24 has a bottom plate protrusion 24a, side plate protrusion 24b, intermediate protrusion 24g, and extension plate protrusion 24c, the first rib-like protrusion may have at least a bottom plate protrusion. That is, the first rib-like protrusion also may be configured form only a bottom plate protrusion, may be configured from a bottom plate protrusion and side plate protrusion, and may be configured from a bottom plate protrusion, side plate protrusion, and extension plate protrusion.

Although side plate protrusions 24b are respectively formed on the pair of side plates 22 in the test piece mounting body 12 shown in FIG. 11 and beyond, the side plate protrusions 24b also may be formed only on one or another of the side plates 22.

Similarly, the intermediate protrusion 24g also may be formed on only either one of the pair of top edge surfaces 22c (and interior side surface 25a). The extension plate protrusion 24c also may be formed only on one or the other of the pair of extension plates 23. The second rib-like protrusion 25 also may be formed only on one or the other of the pair of extension plates 23.

Although the test piece mounting body 12 shown in FIG. 11 and beyond has a pair of first rib-like protrusions 24 and a pair of second rib-like protrusions 25, the number of first rib-like protrusions also may be three or more. The number of second rib-like protrusions also may be three or more. In these cases also the first rib-like protrusion and the second rib-like protrusion preferably are formed in the space in the longitudinal direction of the test piece mounting body.

Although the test piece mounting body 12 has bottom plate 21, side plates 22, and extension plates 23, the test piece mounting body also may be configured with extension plates.

Although, in the test piece mounting body 12, the bottom plate protrusions 24a are rib-like extending in a direction intersecting the longitudinal direction (Y direction) of the bottom plate 21, the shape of the bottom plate protrusion is not limited to this shape and may be, for example, point-like (conical, pyramid-shaped, hemispherical). spherical A plurality of point-like bottom plate protrusions, for example, may be formed side by side along one or more straight lines. The structure of the point-like bottom plate protrusion may be exemplified by a structure configured of first and second protrusion groups. The first and second protrusion groups configure the plurality of point-like bottom plate protrusions side by side along straight lines intersecting the longitudinal direction of the bottom plate. The first and second protrusion groups may be formed in the space in the longitudinal directions of the bottom plate.

Although, in the analyzer 10, the test piece mounting body 12 is mounted to the endless belt 14 by locking the support bar 28 to the holding recess 31 of the interior surface 14a of the endless belt 14, the mounting structure of the test piece mounting body relative to the endless belt is not limited to this structure, and another structure may be used. For example, the test piece mounting body may be mounted on the endless belt through a mounting member having a recess that is fitted to a convex part of the interior surface of the endless belt.

What is claimed is:

1. A test piece analyzer comprising:
a transport device, comprising a plurality of individual test piece mounting bodies and an endless belt extending in a horizontal direction with a horizontal length that is longer than a vertical length in which the belt extends in a vertical direction, wherein the endless belt drives together the plurality of individual test piece mounting bodies, wherein each respective individual test piece mounting body is configured to transport a respective single test piece containing a liquid sample from a first positon to a second position horizontally distanced from the first position, and each respective single test piece is laid sideway on the respective individual test piece mounting body while being transported;
a drive part comprising a motor that drives the endless belt of the transport device;
an imaging device comprising a camera that captures an image of the test piece, while the test piece is mounted on the test piece mounting body, at the second position; and
a casing that houses the transport device, the imaging device, and the drive part, wherein the casing includes a pull-out part of the casing;
wherein the transport device is removably mounted to the pull-out part and is configured to be pulled out and removed from the casing with the pull-out part,
wherein the transport device is formed of water resistant parts for washing when pulled out and removed from the casing,
wherein the pull-out part of the casing has a first connecting part;
wherein the transport device has a second connecting part that is connectable to the first connecting part; and
wherein the transport device is removably mounted to the pull-out part of the casing through the first connecting part and second connecting part.

2. The test piece analyzer of claim 1, wherein the test piece mounting body circulates in conjunction with a circulation of the endless belt.

3. The test piece analyzer of claim 1, wherein each respective individual test piece mounting body is configured to transport the respective single test piece from the first position to the second position horizontally distanced from the first position without changing an orientation of the respective single test piece relative to the casing.

4. The test piece analyzer of claim 1, wherein each respective individual test piece mounting body is configured to transport the respective single test piece from the first position to the second position horizontally distanced from the first position along a portion of the endless belt extending substantially horizontally, wherein the first position and the second position are both located on the portion of the endless belt that extends substantially horizontally.

5. A test piece analyzer that comprises:
a transport device comprising a plurality of individual test piece mounting bodies and an endless belt extending in a horizontal direction with a horizontal length that is longer than a vertical length in which the belt extends in a vertical direction, wherein the endless belt drives together the plurality of individual test piece mounting bodies, wherein each respective individual test piece mounting body transports a respective single test piece from a first position to a second position horizontally distanced from the first position,
a drive part to drive the endless belt of the transport device,
an imaging device to image the respective single test piece while mounted on the test piece mounting body at the second position, and
a casing that houses the transport device, the imaging device, and the drive part, wherein the casing includes a pull-out part of the casing,
wherein the individual test piece mounting body comprises:
a bottom plate capable of mounting the respective single test piece containing a liquid sample which is laid sideway longitudinally in a first direction of the bottom plate while being transported horizontally in a second direction which intersects the first direction; and
a pair of side plates protruding from the bottom plate in a direction of a surface side of the bottom plate from both side edges of the bottom plate across the longitudinal direction of the bottom plate,
wherein a plurality of bottom plate protrusions capable of supporting the respective single test piece are formed on the surface of the bottom plate along the longitudinal direction of the bottom plate,
wherein the transport device is removably mounted to the pull-out part and is configured to be pulled out and removed from the casing with the pull-out part,
wherein the transport device is formed of water resistant parts for washing when pulled out and removed from the casing,
wherein the pull-out part of the casing has a first connecting part,
wherein the transport device has a second connecting part that is connectable to the first connecting part, and
wherein the transport device is removably mounted to the pull-out part of the casing through the first connecting part and second connecting part.

6. The test piece analyzer of claim 5, wherein the plurality of bottom plate protrusions are formed at intervals in the longitudinal direction of the bottom plate, and extend in a direction intersecting the longitudinal direction of the bottom plate.

7. The test piece analyzer of claim 5, wherein at least three bottom plate protrusions are formed on the surface of the bottom plate.

8. The test piece analyzer of claim 5, wherein the bottom plate protrusions have a tapered width shape in the protrusion direction that is capable of supporting the test piece at the apex.

9. The test piece analyzer of claim 5, wherein a space capable of accommodating the test piece on the side of the bottom plate has a distance in the width direction of the bottom plate that is greater than the width of the test piece.

10. The test piece analyzer of claim 5, further comprising:
an extension plate that extends outward from the protruding edge of the side plate wherein one or more extension plate protrusions capable of supporting the respective single test piece are formed on the extension plate on the surface of the protrusion direction side of the side plate, and extend in a direction intersecting the longitudinal direction of the bottom plate.

11. The test piece analyzer of claim 5, wherein
the protruding edge surface of the side plate is an inclined surface facing the opposite direction of the protrusion direction toward the inside.

12. The test piece analyzer of claim 5, wherein
the bottom plate is substantially parallel to the endless belt at a location where the individual test piece mounting body is coupled to the endless belt.

13. A test piece analyzer comprising:
an imaging device to image a test piece;
a transport device that includes a plurality of separate individual test piece mounting bodies which are driven by an endless belt extending in a horizontal direction with a horizontal length that is longer than a vertical length in which the belt extends in a vertical direction, wherein each respective separate individual test piece mounting body transports a respective single test piece containing a liquid sample, and each respective single test piece is laid sideway on the respective separate individual test piece mounting body while being transported from a first position to a second position that is an imaging position of the imaging device where the imaging device images each respective single test piece while mounted on a respective individual test piece mounting body, and wherein the second position is horizontally distanced from the first position;
wherein the transport device comprises a pair of rotating bodies driven by a motor, and the endless belt looped around the rotating bodies, and
the plurality of separate individual test piece mounting bodies for mounting the respective single test pieces are attached independently to the endless belt, so that each of the separate individual test piece mounting bodies are not linked to one another, and the plurality of separate individual test piece mounting bodies form a belt surface in a transport direction before reaching an end of the endless belt;
wherein the test piece analyzer further comprises a casing having a main casing part to house the imaging device, the drive part, and the transport device, wherein the casing includes a pull-out part of the casing;
wherein the transport device is removably mounted to the pull-out part and is configured to be pulled out and removed from the casing with the pull-out part,
wherein the transport device is formed of water resistant parts for washing when pulled out and removed from the casing,
wherein the pull-out part of the casing has a first connecting part,
wherein the transport device has a second connecting part that is connectable to the first connecting part, and
wherein the transport device is removably mounted to the pull-out part of the casing through the first connecting part and second connecting part.

14. The test piece analyzer of claim 13, wherein
at least one edge in the width direction of the bottom surface of the separate individual test piece mounting body is attached to the endless belt.

15. The test piece analyzer of claim 13, wherein
the transport device comprises a guide part to regulate positional displacement of the respective separate individual test piece mounting body from the track of the endless belt when the respective separate individual test piece mounting body is transported by the circulatory movement of the endless belt.

16. The test piece analyzer of claim 13, wherein
the casing has an opening to expose at least a part of the test piece mounting body when the test piece mounting body is at the first position.

* * * * *